United States Patent
Hovey et al.

(10) Patent No.: US 9,040,088 B2
(45) Date of Patent: *May 26, 2015

(54) NANOPARTICULATE MEGESTROL FORMULATIONS

(71) Applicant: Alkermes Pharma Ireland Limited, Dublin 4 (IE)

(72) Inventors: Douglas Hovey, Trooper, PA (US); John Pruitt, Suwanee, GA (US); Tuula Ryde, Malvern, PA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,517

(22) Filed: Nov. 7, 2014

(65) Prior Publication Data

US 2015/0056286 A1  Feb. 26, 2015

Related U.S. Application Data

(60) Division of application No. 10/878,623, filed on Jun. 29, 2004, which is a continuation-in-part of application No. 10/412,669, filed on Apr. 14, 2003, now Pat. No. 7,101,576.

(60) Provisional application No. 60/371,680, filed on Apr. 12, 2002, provisional application No. 60/430,348, filed on Dec. 3, 2002.

(51) Int. Cl.
*A61K 9/14* (2006.01)
*A61K 9/00* (2006.01)
(Continued)

(52) U.S. Cl.
CPC ............... *A61K 9/14* (2013.01); *A61K 9/0095* (2013.01); *A61K 9/10* (2013.01); *A61K 9/145* (2013.01); *A61K 9/146* (2013.01); *A61K 31/57* (2013.01); *A61K 45/06* (2013.01); *A61K 47/20* (2013.01); *A61K 47/32* (2013.01); *A61K 47/38* (2013.01); *A61K 9/08* (2013.01); *A61K 31/573* (2013.01); *A61K 47/26* (2013.01); *A61K 47/34* (2013.01); *A61K 47/42* (2013.01)

(58) Field of Classification Search
CPC ........................................................ A61K 9/14
See application file for complete search history.

(56) References Cited

U.S. PATENT DOCUMENTS 4,783,484 A  11/1988 Violante et al.
4,826,689 A   5/1989 Violanto et al.
(Continued)

FOREIGN PATENT DOCUMENTS

EP   0 338 404       10/1989
EP   338404  A1 *  10/1989
(Continued)

OTHER PUBLICATIONS

Office Action dated Sep. 18, 2008, for related U.S. Appl. No. 10/878,623, 16 pgs.
(Continued)

*Primary Examiner* — Carlos Azpuru
*Assistant Examiner* — Casey Hagopian
(74) *Attorney, Agent, or Firm* — Foley & Lardner LLP

(57) ABSTRACT

The present invention is directed to nanoparticulate compositions comprising megestrol. The megestrol particles of the composition have an effective average particle size of less than about 2000 nm.

29 Claims, 5 Drawing Sheets

(51) Int. Cl.

| | | |
|---|---|---|
| A61K 9/10 | (2006.01) | |
| A61K 31/57 | (2006.01) | |
| A61K 45/06 | (2006.01) | |
| A61K 47/20 | (2006.01) | |
| A61K 47/32 | (2006.01) | |
| A61K 47/38 | (2006.01) | |
| A61K 9/08 | (2006.01) | |
| A61K 31/573 | (2006.01) | |
| A61K 47/26 | (2006.01) | |
| A61K 47/34 | (2006.01) | |
| A61K 47/42 | (2006.01) | |

(56) References Cited

U.S. PATENT DOCUMENTS

| | | |
|---|---|---|
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,338,732 A | 8/1994 | Atzinger |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,449,521 A | 9/1995 | Lovrecich |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,605,889 A | 2/1997 | Curatolo et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |
| 6,028,065 A | 2/2000 | Ragunathan et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,504 A | 12/2000 | Bell |
| 6,165,506 A | 12/2000 | Jain et al. |
| 6,221,400 B1 | 4/2001 | Liversidge et al. |
| 6,264,922 B1 | 7/2001 | Wood et al. |
| 6,267,989 B1 | 7/2001 | Liversidge et al. |
| 6,268,356 B1 | 7/2001 | Ragunathan et al. |
| 6,270,806 B1 | 8/2001 | Liversidge et al. |
| 6,316,029 B1 | 11/2001 | Jain et al. |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,593,318 B2 | 7/2003 | Ragunathan |
| 6,593,320 B2 | 7/2003 | Ragunathan |
| 6,656,505 B2 | 12/2003 | Kundu et al. |
| 6,833,373 B1 | 12/2004 | McKearn et al. |
| 2002/0012675 A1 | 1/2002 | Jain et al. |
| 2002/0028794 A1* | 3/2002 | Brubaker et al. ............ 514/177 |
| 2002/0131988 A1 | 9/2002 | Foster et al. |
| 2003/0045563 A1 | 3/2003 | Gao et al. |
| 2003/0108575 A1 | 6/2003 | Lu |
| 2003/0219490 A1 | 11/2003 | Hovey et al. |
| 2005/0233001 A1 | 10/2005 | Hovey et al. |
| 2010/0226989 A1 | 9/2010 | Hovey et al. |
| 2012/0087955 A1 | 4/2012 | Hovey et al. |

FOREIGN PATENT DOCUMENTS

| | | |
|---|---|---|
| EP | 0 371 431 | 6/1990 |
| EP | 0 499 299 | 8/1992 |
| EP | 0 577 215 | 1/1994 |
| JP | 2001-316274 | 11/2001 |
| WO | WO 93/25190 | 12/1993 |
| WO | WO 96/24336 | 8/1996 |
| WO | WO 97/10814 | 3/1997 |
| WO | WO 99/43359 | 9/1999 |
| WO | WO 00/56366 | 9/2000 |
| WO | WO 00/72973 | 12/2000 |
| WO | WO 01/12229 | 2/2001 |
| WO | WO 01/17546 A1 | 3/2001 |
| WO | WO 01/91750 | 12/2001 |
| WO | WO 01/97779 | 12/2001 |
| WO | WO 02/094215 A2 | 11/2002 |
| WO | WO 02/098565 | 12/2002 |
| WO | WO 03/002097 | 1/2003 |
| WO | WO 03/086354 A1 | 10/2003 |
| WO | WO 2004/041246 | 5/2004 |
| WO | WO 2004/050059 | 6/2004 |
| WO | WO 2005/044234 | 5/2005 |

OTHER PUBLICATIONS

European Office Action issues for European Application No. 03 723 991.0 dated Nov. 4, 2008, 9 pgs.

Gaver et al., "Liquid Chromatographic Procedure for the Quantitative Analysis of Megestrol Acetate in Human Plasma", *Journal of Pharmaceutical Sciences*, vol. 74, No. 6, pp. 664-667 (Jun. 1985).

Lindahl et al., "Characterization of Fluids from the Stomach and Proximal Jejunum in Men and Women", *Pharmaceutical Research*, vol. 14, No. 4, pp. 497-502 (1997).

*Stedman's Medical Dictionary*, 25th Edition, p. 935 (1990).

Office Action cited in related U.S. Appl. No. 11/472,556, dated Mar. 31, 2009.

Office Action cited in related U.S. Appl. No 11/472,556, dated Jul. 23, 2009, 34 pgs.

Eurasia Office Action dated Jun. 23, 2009, cited in related Eurasia Application No. 200800099/28, 3 pgs.

Office Action cited in related U.S. Appl. No. 10/878,623, dated Sep. 29, 2009.

Office Action cited in related U.S. Appl. No. 11/093,149, dated Sep. 24, 2009.

Office Action cited in related U.S. Appl. No. 11/979,253, dated Sep. 29, 2009.

Notice of Rejections for JP 2004-570751 dated Dec. 21, 2009, 3 pgs.

(56) References Cited

OTHER PUBLICATIONS

U.S. Office Action in related U.S. Appl. No. 10/420,927, dated Dec. 10, 2009.
Notice of Rejections for JP 2003-583377 dated Dec. 22, 2009, 5 pgs.
Office Action cited in related U.S. Appl. No. 11/093,149, dated May 13, 2010.
Graham, K. K., D. J. Mikolich, et al. (1994). "Pharmacologic evaluation of megestrol acetate oral suspension in cachectic AIDS patients." J Acquir Immune Defic Syndr 7(6): 580-6.
Academy of Managed Care Pharmacy; A Format for Submission of Clinical and Economic Data in Support of Formulary consideration by Health Care Systems in the United States; Format for Formulary Submissions, Oct. 2002.
Aisner, J., H. Parnes, et al. (1990). "Appetite stimulation and weight gain with megestrol acetate." Semin Oncol 17(6 Suppl 9): 2-7.
Alakhov, V., G. Pietrzynski, et al. (2004). "Pluronic block copolymers and Pluronic poly(acrylic acid) microgels in oral delivery of megestrol acetate." J Pharm Pharmacol 56(10): 1233-41.
Alexander, et al.; Medical Care at the End of life; Health Resources and Services Administration Chapter 24, pp. 493-503.
Alexander, et al.; Special Populations; Health Resources and Services Administration Chapter 15, pp. 315-327.
Appendix B: Cornell Scale of Depression in Dementia, reprinted from Alexopoulos, G.S. et al., "Cornell Scale for Depression in Dementia" Biol Psychiatry Feb. 1988; 23(3):271-84.
Baraia-Etxaburu, A.J. et al., Primary adrenal failure and AIDS: report of 11 cases and review of the literature. Rev Clin Esp. Feb. 1998; 198(2):74-9.
Barini-Garcia, Magda; Resources, Health Resources and Services Administration Chapter 26, pp. 515-548.
Batterham, M. J. And R. Garsia (2001). "A comparison of megestrol acetate, nandrolone decanoate and dietary counselling for HIV associated weight loss." Int J Androl 24(4): 232-40.
Beal, et al.; Long-Term Efficacy and Safety of Dronabinol for Acquired Immunodeficiency Syndrome-Associated Anorexia; Journal of Pain and Symptom Management 1997; 14(1):7-14.
Beal, J. and N. Flynn (1995). "AIDS-associated anorexia." J Physicians Assoc AIDS Care 2(1): 19-22.
Beehler, MD, Connie J.; U.S. Department of Health and Human Services, Chapter 6, pp. 135-155.
Beller, E., M. Tattersall, et al. (1997). "Improved quality of life with megestrol acetate in patients with endocrine-insensitive advanced cancer: a randomised placebo-controlled trial. Australasian Megestrol Acetate Cooperative Study Group." Ann Oncol 8(3): 277-83.
Bentley, et al.; AIDS and Long-Term Care Facilities; Topics in Long-Term Care 1990; 11:202-206.
Berenstein, EG, et al.; Megestrol acetate for the treatment of anorexia-cachexia syndrome (Review); The Cochrane Library 2005, Issue 2:1-37.
Berger, et al.; Oxandrolone in AIDS-Wasting Myopathy; AIDS 1996; 10:1657-1662.
Bhasin, et al.; Effects of Testosterone Replacement with a Nongenital, Transdermal System, Androderm, in Human Immunodeficiency Virus-Infected Men with Low Testosterone Levels; Journal of Endocrinology and Metabolism 1998; 83(9):3155-3162.
Biggar, et al.; Epidemiology and Social Science; Cancer Risk in Eldery Person With HIV/AIDS; J Acquir Immune Defic Syndr 2004; 36(3):861-868.
Blaum, et al.; Factors Associated With Low Body Mass Index and Weight Loss in Nursing Home Residents; Journal of Gerontology: Medical Services 1995; 50A(3):M162-M168.
Brambilla, G. and A. Martelli (2002). "Are some progestins genotoxic liver carcinogens?" Mutat Res 512(2-3): 155-63.
Breithart, MD, William; U.S. Department of Health and Human Services, Chapter 4, pp. 85-122.
Bristol-Myers Squibb; Megace, Bristol-Myers Squibb Oncology, 2002, pp. 1-5.
British Library, The; AIDS Policy & Law, 2004.
Bruera, E., K. Macmillan, et al. (1990). "A controlled trial of megestrol acetate on appetite, caloric intake, nutritional status, and other symptoms in patients with advanced cancer." Cancer 66(6): 1279-82.
Bruera, E., S. Ernst, et al. (1998). "Effectiveness of megestrol acetate in patients with advanced cancer: a randomized, double-blind, crossover study." Cancer PrevControl 2(2): 74-8.
Buchanan, et al.; Analyses of Nursing Home Residents with Human Immunodeficiency Virus and Depression Using the Minimum Data Set; AIDS Patient Care and STDs 2002; 16(9):441-455.
Buchanan, et al.; Profiles of Nursing Home Residents with HIV; Journal of Health Care for the Poor and Underserved 2002; 13(3):379-391.
Camaggi, C. M., E. Strocchi, et al. (1995). "Pharmacokinetic evaluation of two different formulations of megestrol acetate in patients with advanced malignancies." Cancer Chemother Pharmacol 36(4): 356-9.
Cancer consultants.com; Thalomid® Palliates Cancer-Related Cachexia, Apr. 2005.
Castro, MD, Kenneth, et al.; 1993 Revised Classification System for HIV Infection and Expanded Surveillance Case Definition for AIDS Among Adolescents and Adults, www.cdc.gov; 1993, 15 pp.
Cella, D. F., J. VonRoenn, et al. (1995). "The Bristol-Myers Anorexia/Cachexia Recovery Instrument (BACRI): a brief assessment of patients' subjective response to treatment for anorexia/cachexia." Qual Life Res 4(3): 221-31.
Chapman, Karen M.; Loss of appetite: managing unwanted weight loss in the older patient; Geriatrics 1994; 49(3):54-59.
Chen, H. C., S. W. Leung, et al. (1997). "Effect of megestrol acetate and prepulsid on nutritional improvement in patients with head and neck cancers undergoing radiotherapy." Radiother Oncol 43(1): 75-9.
Chlebowski, et al.; Nutritional Status, Gastrointestinal Dysfunction, and Survival in Patients with AIDS; The American Journal of Gastroenterology 1989; 84(10):1288-1293.
Christeff, N. et al. Changes in cortisol/DHEA ration in HIV-infected men are related to immunological and metabolic perturbations leading to malnutrition and lipodystrophy. Annals NY Acad Sc. 2000; 917:962-70.
Christeff, N. Serum cortisol and DHEA concentrations during HIV infection. Psychoneuroendocrinology. 1997; 22 Suppl 1:S11-8.
Clerici M. et al., A possible role for the cortisol/anticortisols imbalance in the progression of human immunodeficiency virus; Psychoneuroendocrinology. 1997; 22 Suppl 1:S27-31.
Clerici, M. et al. Immunoendocrinologic abnormalities in human immunodeficiency virus infection. Ann NY Acad Sci. 2000; 917:956-61.
Cloud, et al.; Newly diagnosed HIV infection in an octogenarian; the elderly are not 'immune'; Age and Ageing 2003; 32(3):353-354.
Coodley, G. O., M. O. Loveless, et al. "The HIV wasting syndrome: a review." J Acquir Immune Defic Syndr 7(7): 681-94.
Corcoran, C. and S. Grinspoon (1999). "Treatments for wasting in patients with the acquired immunodeficiency syndrome." N Engl J Med 340(22): 1740-50.
Council for Nutrition; Clinical Guide to Prevent and Manage Malnutrition in Long-Term Care for Nursing Staff and Dietary Staff and Dietitians (Evaluate, Document and Treat); Programs in Medicine (Rev. Sep. 8, 2000).
Cragle, et al.; Risk Factors Associated with the Classification of Unspecified and/or Unexplained Causes of Death in an Occupational Cohort; American Journal of Public Health Mar. 1992; 82(3):455.
Curtis, J. Randall; Patient-Clinician Communication; Chapter 21, pp. 431-445, Health Resources and Services Administration.
Dahele, M. and K. C. Fearon (2004). "Research methodology: cancer cachexia syndrome." Palliat Med 18(5): 409-17.
Davis, M. P. and D. Dickerson (2000). "Cachexia and anorexia: cancer's covert killer." Support Care Cancer 8(3): 180-7.
Davis, Mellar P., et al.; Appetite and Cancer-Associated Anorexia: A Review; Journal of Clinical Oncology Apr. 15, 2004; 22(8):1510-1517.
De Conno, F., C. Martini, et al. (1998). "Megestrol acetate for anorexia in patients with far-advanced cancer: a double-blind controlled clinical trial." Eur J Cancer 34(11): 1705-9.

(56) References Cited

OTHER PUBLICATIONS

Delmore, G. (2000). "Cachexia—quo vadis?" Support Care Cancer 8(3): 165-6.
Desport, JC; Standards, Options and Recommendations for the use of appetite stimulants in oncology, British Journal of Cancer 2003; 89:S98-S100.
Dobs, MD, Adrian, et al.; Endocrine Disorders in Men Infected with Human Immunodeficiency Virus, The American Journal of Medicine 1988, 84:611-616.
Dore, M.X., et al. Peripheral adrenal insufficiency in AIDS. Rev Med Interne. Jan. 1998; 19(1):23-8.
Duc, I., J. Botella, et al. (1995). "Antiandrogenic properties of nomegestrol acetate." Arzneimittelforschung 45(1): 70-4.
Edmunds-Ogbuokiri, Justina; Pharmacologic Interactions of Clinical Significance; Health Resources and Services Administration; Chapter 27, pp. 549-602.
Eledrisi, M.S. and Verghese, A.C. Adrenal insufficiency in HIV infection: a review and recommendations. Am. J. Med. Sci. Feb. 2001; 321(2):137-44.
Ensrud, K. E., S. K. Ewing, et al. (2003). "Intentional and unintentional weight loss increase bone loss and hip fracture risk in older women." J Am Geriatr Soc 51(12): 1740-7.
Erkurt, E., M. Erkisi, et al. (2000). "Supportive treatment in weight-losing cancer patients due to the additive adverse effects of radiation treatment and/or chemotherapy." J Exp Clin Cancer Res 19(4): 431-9.
Eubanks, V., N. Koppersmith, et al. (2002). "Effects of megestrol acetate on weight gain, body composition, and pulmonary function in patients with cystic fibrosis." J Pediatr 140(4): 439-44.
Fantoni, M., et al.; Symptom Profile in Terminally Ill AIDS Patients; AIDS Patient Care and STDs 1996; 10(3):171-173.
Farinha, A., A. Bica, et al. (2000). "Improved bioavailability of a micronized megestrol acetate tablet formulation in humans." Drug Dev Ind Pharm 26(5): 567-70.
Feliu, J., M. Gonzalez-Baron, et al. (1992). "Usefulness of megestrol acetate in cancer cachexia and anorexia. A placebo-controlled study." Am J Clin Oncol 15(5): 436-40.
Femia, R. A. and R. E. Goyette (2005). "The science of megestrol acetate delivery: potential to improve outcomes in cachexia." BioDrugs 19(3): 179-87.
Fermia, Robert A., Megestrol Acetate Nanocrystal Oral Suspension: Results of Dose-Escalating Studies Under Fed and Fasting Conditions, Poster #0106, Presented at the National HIV/AIDS Update Conference, Oakland, California, Apr. 10-13, 2005.
Fields, Sheldon D., et al.; The Physiologic Health Care Needs of HIV-Infected Black Men on Admission to an AIDS-Dedicated Nursing Home, Journal of the Association of Nurses in AIDS Care Jan./Feb. 2003; 14(1):63-72.
Fields, Sheldon D., The Love and Belonging Healthcare Needs of HIV Infected African-American Men Upon Admission to an AIDS Dedicated Nursing Home, Journal of National Black Nurses Association Jun. 2003; 14(1):38-44.
Fietkau, R., M. Riepl, et al. (1997). "Supportive use of megestrol acetate in patients with head and neck cancer during radio(chemo)therapy." Eur J Cancer 33(1): 75-9.
Flegal, Katherine M., et al.; Excess Deaths Associated with Underweight, Overweight, and Obesity, JAMA 2005, Apr. 20; 293(15):1861-7.
Flint, A., et al.; Reproducibility, power and validity of visual analogue scales in assessment of appetite sensations in single test meal studies; International Journal of Obesity 2000; 24:38-48.
Foley, et al.; Palliative Care in Resource-Poor Settings; Health Resources and Services Administration Chapter 19, pp. 387-407.
Folstein, et al.; "Mini-Mental State" A Practical Method for Grading the Cognitive State of Patients for the Clinician; J. Psychiat. Res. 1975; 12:189-198.
Forrester, et. al.; Weight loss and body-composition changes in men and women infected with HIV; Am J Clin Nutr. 2002; 76(6):1428-1434.
Forstein, MD, Marshall, Psychiatric Problems, U.S. Department of Health and Human Services, Chapter 10, pp. 207-252.

Gabbard, Dee, et al.; Oncology Nutrition Standards of Care; Integrating Nutrition Into Your Cancer Program, Mar./Apr. 2002, pp. 8-10.
Gaver, R. C., K. A. Pittman, et al. (1985). "Bioequivalence evaluation of new megestrol acetate formulations in humans." Semin Oncol 12(1 Suppl 1): 17-9.
Gayer, R. C., K. A. Pittman, et al. (1986). "Evaluation of two new megestrol acetate tablet formulations in humans." Biopharm Drug Dispos 7(1): 35-46.
Gebbia, V., A. Testa, et al. (1996). "Prospective randomised trial of two dose levels of megestrol acetate in the management of anorexia-cachexia syndrome in patients with metastatic cancer." Br J Cancer 73(12): 1576-80.
Gebo, Kelly A., et al.; Treatment of HIV infection in the older patient; Expert Rev. Anti Infect. Ther. 2004; 2(5):733-43.
Giacosa; et al.; Changes of nutritional and psychological status after megestrol acetate treatment of cancer cachexia; Rivista Italian di Nutrizione Parenterale ed Enterale 1997; 15(1):20-23.
Glatt, Aaron E., et al.; Successful Implementation of a Long-term Care Unit for Patients with Acquired Immunodeficiency Syndrome in an Underserved Suburban Area With a High Incidence of Human Immunodeficiency Virus; Arch Internal Medicine Apr. 1992; 152:823-825.
Gordon, Sandra; Weighing in: Preventing Cancer Weight Loss, Cure-Summer 2003 (curetoday.com) pp. 42-47.
Greenwald, Robert; Legal and Financial Issues; Health Resources and Services Administration; Chapter 18, pp. 365-386.
Grinspoon, S. and K. Mulligan (2003). "Weight loss and wasting in patients infected with human immunodeficiency virus." Clin Infect Dis 36(Suppl 2): S69-78.
Grinspoon, S., C. Corcoran, et al. (1996). "Loss of lean body and muscle mass correlates with androgen levels in hypogonadal men with acquired immunodeficiency syndrome and wasting." J Clin Endocrinol Metab 81(11): 4051-8.
Grunfeld, Carl, et al.; Resting energy expenditure, caloric intake, and short-term weight change in human immunodeficiency virus infection and the acquired immunodeficiency syndrome; American Journal of Clinical Nutrition 1992; 55:455-60.
Haslett, Patrick; The Metabolic and Immunologic Effects of Short-Term Thalidomide Treatment of Patients Infected with the Human Immunodeficiency Virus; AIDS Research and Human Retroviruses Nov. 12, 1997; 13(12):1047-1054.
Health & Medicine Week; Pharma Company Receives FDA Fast track Status for Anorexia/ Cachexia Treatment; www.newsrx.com Feb. 7, 2005; pp. 261-262.
Heath, John Michael; Care of Persons with AIDS in the Nursing Home; Family Medicine Jun. 1998; 30(6):436-440.
Heckmayr, M. and U. Gatzemeier (1992). "Treatment of cancer weight loss in patients with advanced lung cancer." Oncology 49 Suppl 2: 32-4.
Hellerstein, M.D., Marc, et al. HIV-Associated Wasting Syndrome and Body-Habitus Changes. The PRN Notebook Sep. 1998; 3(3):14-21.
Hoshino, Y. et al. Cytomegalovirus (CMV) retinitis and CMV antigenemia as a clue to impaired adrenocortical function in patient with AIDS. AIDS Nov. 15, 1997; 11(14):1719-24.
Hudgens, Jan, et al.; Immune Function is Impaired with a Mini Nutritional Assessment Score Indicative of Malnutrition in Nursing Home Elders with Pressure Ulcers; Journal of Parenteral and Enteral Nutrition 2004; 28(6):416-422.
Huffman, G. B. (2002). "Evaluating and treating unintentional weight loss in the elderly." Am Fam Physician 65(4): 640-50.
Hurtado, MD, Rocio, et al.; U.S. Department of Health and Human Services, Chapter 5, pp. 123-133.
Hutton, et al.; The Care of Children and Adolescents; A Clinical Guide to Supportive and Palliative Care for HIV/AIDS; Chapter 12, pp. 267-288.
Iarussi, Diana, et al.; Anthracycline-Induced Cariotoxicity in Children With Cancer; Leading Article, Pediatric Drugs 2005; 7:67-76.
Ingham, et al.; Assessment of Physical Symptoms; U.S. Department of Health and Human Services, Health Resources and Services Administration, HIV/AIDS Bureau Chapter 3, pp. 37-83.
Inui, A. (2002). "Cancer anorexia-cachexia syndrome: current issues in research and management." CA Cancer J Clin 52(2): 72-91.

(56) References Cited

OTHER PUBLICATIONS

Jansen, et al.; Ethical Issues; Health Resources and Services Administration Chapter 17, pp. 349-364.
Jatoi, A., H. E. Windschitl, et al. (2002). "Dronabinol versus megestrol acetate versus combination therapy for cancer-associated anorexia: a North Central Center Treatment Group study." J Clin Oncol 20(2): 567-73.
Jatoi, A., K. Rowland, et al, (2004). "An eicosapentaenoic acid supplement versus megestrol acetate versus both for patients with cancer-associated wasting: a North Central Cancer Treatment Group and National Cancer Institute of Canada collaborative effort." J Clin Oncol 22(12): 2469-76.
Jatoi, A., S. Kumar, et al. (2000). "On appetite and its loss." J Clin Oncol 18(15): 2930-2.
Kaplan, G., S. Thomas, et al. (2000). "Thalidomide for the treatment of AIDS-associated wasting." AIDS Res Hum Retroviruses 16(14): 1345-55.
Karcic, E., C. Philpot, et al. (2002). "Treating malnutrition with megestrol acetate: literature review and review of our experience." J Nutr Health Aging 6(3): 191-200.
Kaufmann, M., E. Bajetta, et al. (2000). "Exemestane improves survival compared with megoestrol acetate in postmenopausal patients with advanced breast cancer who have failed on tamoxifen. results of a double-blind randomised phase III trial." Eur J Cancer 36 Suppl 4: S86-7.
Kaufmann, M., E. Bajetta, et al. (2000). "Exemestane is superior to megestrol acetate after tamoxifen failure in postmenopausal women with advanced breast cancer: results of a phase III randomized double-blind trial. The Exemestane Study Group." J Clin Oncol 18(7): 1399-411.
Kennedy, Deborah H., et al.; Retrospective Review of Megestrol Use for Weight Loss in an Elderly Veteran Population; The Consultant Pharmacist Apr. 2005; 20(4):301-305.
Klein, Waldo C., et al.; Residents with AIDS: A Comparison of Facilities with Experience and Those Without, AIDS Patent Care and STDs 1997; 11(4):277-284.
Kotler, D. (2004). "Challenges to Diagnosis of HIV-Associated Wasting." J Acquir Immune Defic Syndr 37: S280-S283.
Kotler, D. and C. Wanke (2004). "Management of HIV Wasting Syndrome: A Consensus Conference." J Acquir Immune Defic Syndr 37: S261.
Kotler, D. P. (2000). "Cachexia." Ann Intern Med 133(8): 622-34.
Kouba, MD, David J.; Dermatologic Problems, Chapter 9; U.S. Department of Health and Human Services, pp. 177-206.
Krentz, Andrew J., et al.; Anthropometric, Metabolic, and Immunological Effects of Recombinant Human Growth Hormone in AIDS and AIDS-Related Complex; Journal of Acquired Immune Deficiency Syndromes 1993; 6:245-251.
Kropsky, B., Y. Shi, et al. (2003). "Incidence of deep-venous thrombosis in nursing home residents using megestrol acetate." J Am Med Dir Assoc 4(5): 255-6.
Kropsky, et al.; Author's Response to Letter; J Am Med Dir Assoc Jan./Feb. 2004; 5(1):66-67.
Kutzen, et al.; Facilitating the Transition to Home-Based and Hospice Care; Health and Services Administration Chapter 22, pp. 447-477.
Lai, Y. L., F. M. Fang, et al. (1994). "Management of anorexic patients in radiotherapy: a prospective randomized comparison of megestrol and prednisolone." J Pain Symptom Manage 9(4): 265-8.
Lalonde, Bernadette, et al.; Delirium in AIDS Patients: Discrepancy between Occurrence and Health Care Provider Identification; AIDS Patient Care and STDs Nov. 5, 1996; 10(5):282-287.
Lambert, C. P., D. H. Sullivan, et al. (2002). "Effects of testosterone replacement and/or resistance exercise on the composition of megestrol acetate stimulated weight gain in elderly men: a randomized controlled trial." J Clin Endocrinol Metab 87(5): 2100-6.
Lambert, C. P., M. G. Flynn, et al. (2004). "Effects of megestrol acetate on circulating interleukin-15 and interleukin-18 concentrations in healthy elderly men." J Gerontol a Biol Sci Med Sci 59(8): 855-8.

Launer, Lenore J., et al.; Body Mass Index, Weight Change, and Risk of Mobility Disability in Middle-aged and Older Women, JAMA Apr. 13, 1994; 271(14):1093-1098.
Lavin, MD, C., et al.; Follow-up of Abnormal Papanicolaou Smears in a Hospital-Based Adolescent Clinic; Journal Pediatric Adolescent Gynecology 1997; 10:141-145.
Lehtimaki, Terbo, et al.; Interleukin-6 Modulates Plasma Cholesterol and C-Reactive Protein Concentrations in Nonagenarians; J Am. Geriatr. Soc. Jun. 2005; 0(0):1-7 (available online at www.blackwell-synergy.com).
Leinung, M. C., R. Liporace, et al. (1995). "Induction of adrenal suppression by megestrol acetate in patients with AIDS." Ann Intern Med 122(11): 843-5.
Lelli, G., M. Montanari, et al. (2003). "Treatment of the cancer anorexia-cachexia syndrome: a critical reappraisal." J Chemother 15(3): 220-5.
Linsk, Nathan L., et al.; The AIDS Epidemic: Challenges for Nursing Homes; Journal of Gerontological Nursing 1993; 19(1):11-22.
Lofgren, L., B. Wallberg, et al. (2004). "Tamoxifen and megestrol acetate for postmenopausal breast cancer: diverging effects on liver proteins, androgens, and glucocorticoids." Med Oncol 21(4): 309-18.
Loprinzi, C. L., A. M. Bernath, et al. (1994). "Phase III evaluation of 4 doses of megestrol acetate as therapy for patients with cancer anorexia and/or cachexia." Oncology 51 Suppl 1: 2-7.
Loprinzi, C. L., D. J. Schaid, et al. (1993). "Body-composition changes in patients who gain weight while receiving megestrol acetate." J Clin Oncol 11(1): 152-4.
Loprinzi, C. L., J. C. Michalak, et al. (1993). "Phase III evaluation of four doses of megestrol acetate as therapy for patients with cancer anorexia and/or cachexia." J Clin Oncol 11(4): 762-7.
Loprinzi, C. L., J. W. Kugler, et al. (1999). "Randomized comparison of megestrol acetate versus dexamethasone versus fluoxymesterone for the treatment of cancer anorexia/cachexia." J Clin Oncol 17(10): 3299-306.
Loprinzi, C. L., N. M. Ellison, et al. (1990). "Alleviation of cancer anorexia and cachexia: studies of the Mayo Clinic and the North Central Cancer Treatment Group." Semin Oncol 17(6 Suppl 9): 8-12.
Loprinzi, C. L., N. M. Ellison, et al. (1990). "Controlled trial of megestrol acetate for the treatment of cancer anorexia and cachexia." J Natl Cancer Inst 82(13): 1127-32.
Lortholary, O. et al., Hypothalamo-pituitary-adrenal function in human immunodeficiency virus-infected men. J. Clin Endocrinol Metab. Feb. 1996; 81(2):791-6.
Lundgren, S. and P. E. Lonning (1990). "Influence of progestins on serum hormone levels in postmenopausal women with advanced breast cancer—II. A differential effect of megestrol acetate and medroxyprogesterone acetate on serum estrone sulfate and sex hormone binding globulin." J Steroid Biochem 36(1-2): 105-9.
Lundholm, Kent, et al.; Palliative nutritional Intervention in Addition to Cyclooxygenase and Erythropoietin Treatment for Patients with Malignant Effects on Survival, Metabolism, and Function; 2004, Wiley InterScience, pp. 1967-1977.
MacDonald, N., A. M. Easson, et al. (2003). "Understanding and managing cancer cachexia." J Am Coll Surg 197(1): 143-61.
Mack, Karin A., et al; AIDS and Older Americans at the End of the Twentieth Century; Journal of Acquired Immune Deficiency Syndromes 2003; 33:S68-S75.
Manfredi, Roberto; Impact of HIV infection and antiretroviral therapy in the older patient; Expert Rev. Anti Infect. Ther. 2004; 2(6):821-824.
Mann, M., E. Koller, et al. (1997). "Glucocorticoidlike activity of megestrol. A summary of Food and Drug Administration experience and a review of the literature." Arch Intern Med 157(15): 1651-6.
Mann, M., et al.; Abstract for Reference 73 of "Causes and pathophysiology of Cushing's syndrome", www.utdol.com; 1 Page
Mantovani, G. (2000). "Cachexia and anorexia." Support Care Cancer 8(6): 506-7.
Mantovani, G., A. Maccio, et al. (1997). "Medroxyprogesterone acetate reduces the in vitro production of cytokines and serotonin involved in anorexia/cachexia and emesis by peripheral blood mononuclear cells of cancer patients." Eur J Cancer 33(4): 602-7.

(56) References Cited

OTHER PUBLICATIONS

Mantovani, G., A. Maccio, et al. (1998). "Cytokine activity in cancer-related anorexia/cachexia: role of megestrol acetate and medroxyprogesterone acetate." Semin Oncol 25(2 Suppl 6): 45-52.

Mantovani, Giovanni, et al; Managing Cancer-Related Anorexia/Cachexia; Drugs 2001; 61(4):499-514.

Markman, M., A. Kennedy, et al. (2000). "Phase I trial of paclitaxel plus megestrol acetate in patients with paclitaxel-refractory ovarian cancer." Clin Cancer Res 6(11): 4201-4.

Matin, K., M. J. Egorin, et al. (2002). "Phase I and pharmacokinetic study of vinblastine and high-dose megestrol acetate." Cancer Chemother Pharmacol 50(3): 179-85.

McCarthy, D. O. (2003). "Rethinking nutritional support for persons with cancer cachexia." Biol Res Nurs 5(1): 3-17.

McCormack, Paula; Undernutrition in the elderly population living at home in the community: a review of the literature, Journal of Advanced Nursing 1997; 26:856-863.

McKinley, Maryann J., et al.; Improved body weight status as a result of nutrition intervention in adult, HIV-positive outpatients, Journal of the American Dietetic Association Nov. 9, 1994; 94(9):1014-1017.

McMillan, D. C., P. O'Gorman, et al. (1997). "A pilot study of megestrol acetate and ibuprofen in the treatment of cachexia in gastrointestinal cancer patients." Br J Cancer 76(6): 788-90.

McMillan, D. C., S. J. Wigmore, et al. (1999). "A prospective randomized study of megestrol acetate and ibuprofen in gastrointestinal cancer patients with weight loss." Br J Cancer 79(3-4): 495-500.

McMillan, et al.; Effect of megestrol acetate on weight loss, body composition and blood screen of gastrointestinal cancer patients; Clinical Nutrition 1994; 13:85-89.

McQuellon, R. P., D. B. Moose, et al. (2000). "Prophylactic megestrol acetate (Megace) in head & neck and lung cancer patients receiving radiation therapy: effect on weight, quality of life (QOL), and toxicity in a phase III placebo controlled trial." Int J Radiat Oncol Biol Phys 48(3 Supplement 1):184.

McQuellon, R. P., D. B. Moose, et al. (2000). "Supportive use of megestrol acetate (Megace) with head/neck and lung cancer patients receiving radiation therapy." Int J Radiat Oncol Biol Phys 52(5): 1180-5.

Meacham, L. R., C. Mazewski, et al. (2003). "Mechanism of transient adrenal insufficiency with megestrol acetate treatment of cachexia in children with cancer." J Pediatr Hematol Oncol 25(5): 414-7.

Meyers, et al.; Medical Care in Advanced AIDS; Health Resources and Services Administration Chapter 23, pp. 479-491.

Morley, et al.; Appetite and Orexigenic Drugs; Annals of Long Term Care, Oct. 2001; 9(Suppl II):1-12; available at www.LTCnutrition.org.

Morley, et. al.; Anorexia in the Elderly: An Update; Annals of Long-Term Care 2001; 9:1-13; available at www.LTCnutrition.org.

Morley, J. E. (2002). "Orexigenic and anabolic agents." Clin Geriatr Med 18(4): 853-66.

Morley, J.E. and Silver, A.J. Nutritional Issues in Nursing Home Care. Ann Internal Medicine; Dec. 1995; 123(11):850-59.

Morley, J.E.; Nutrition is Busting Out All Over, The Journal of Nutrition, Health & Aging 2005; 9(3):131.

Morley, John E., et al.; Development of Guidelines for the Use of Orexigenic Drugs in Long-Term Care; Annals of Long-Term Care; Jun. 2004 (Suppl), available at www.LTCnutrition.org.

Morley, John E., et al.; Nitric Oxide Synthase Inhibition and Food Intake: Effects on Motivation to Eat and in Female Mice; Pharmacology Biochemistry and Behavior 1995; 50(3):369-373.

Morley, John E.; Editorial: Anorexia and Weight loss in Older Persons; Journal of Gerontology, Medical Sciences 2003; 58A(2):131-37.

Moyle, Graeme J., et al.; Efficacy of Selected Treatments of HIV Wasting: A Systematic Review and Meta-Analysis; Journal of Acquired Immune Deficiency Syndrome 2004; 37(Suppl 5):S262-S276.

Murden, R. A. and N. K. Ainslie (1994). "Recent weight loss is related to short-term mortality in nursing homes." J Gen Intern Med 9(11): 648-50.

Muscaritoli, M., M. Bossola, et al. (2004). "Therapy of muscle wasting in cancer: what is the future?" Curr Opin Clin Nutr Metab Care 7(4): 459-66.

Mwamburi, D. M., J. Gerrior, et al. (2004). "Comparing megestrol acetate therapy with oxandrolone therapy for HIV-related weight loss: similar results in 2 months." Clin Infect Dis 38(6): 895-902.

Mwamburi, D. Mkaya, et al.; Combination Megestrol Acetate, Oxandrolone, and Dietary Advice Restores Weight in Human Immunodeficiency Virus; Nutrition in Clinical Practice 2004; 19:395-402.

Naing, K. K., J. A. Dewar, et al. (1999). "Megestrol acetate therapy and secondary adrenal suppression." Cancer 86(6): 1044-9.

Nelson, Kristine; A Phase II Study of Delta-9-Tetrahydrocannabinol for Appetite Stimulation in Cancer-Associated Anorexia, Journal of Pallative Care 1994; 10(1):14-18.

Nemechek, P. M., B. Polsky, et al. (2000). "Treatment guidelines for HIV-associated wasting." Mayo Clin Proc 75(4): 386-94.

Neri, Bruno, et al.; The Role of Megastrol Acetate in Neoplastic Anorexia and Cachexia; Current Therapeutic Research Feb. 1995; 56(2):183-189.

Neumann, Peter J.; Evidence-Based and Value-Based Formulary Guidelines; Health Affairs Jan./Feb. 2004; 23(1):124-134.

New MegaceES, megestrol acetate nanocrystal, 575 mg/5 mL oral suspension (advertisement), 4 pp.

Nieman, MD, Lynnette K.; Causes and pathophysiology of Cushing's syndrome, UpToDate; www.utdol.com; 2005, 14 pp.

Norbiato, G. et al. Glucocorticoids and the immune function in the human immunodeficiency virus infection: a study in hypercortisolemic and cortisol-resistant patients. J Clin Endocrinol Metab. Oct. 1997; 82(10):3260-3.

O'Neill, et al.; HIV and Palliative Care; Chapter 1, pp. 1-3; U.S. Department of Health and Human Services, Health Resources and Services Administration, HIV/AIDS Bureau.

O'Neill, et al.; Care for the Caregiver; Health Resources and Services Administration Chapter 20, pp. 409-429.

O'Neill, et. al.; Substance Use Problems; A Clinical Guide to Supportive and Palliative Care for HIV/AIDS Chapter 11, pp. 253-265.

Omnicare, Inc.; Weight Loss: Agents Promoting Weight Gain, 2005, pp. 609-614.

Orme, L. M., J. D. Bond, et al. (2003). "Megestrol acetate in pediatric oncology patients may lead to severe, symptomatic adrenal suppression." Cancer 98(2): 397-405.

Osoba, D., N. Murray, et al. (1994). "Phase II trial of megestrol in the supportive care of patients receiving dose-intensive chemotherapy." Oncology (Williston Park) 8(3): 43-9; discussion 49-50, 52.

Oster, M. H., S. R. Enders, et al. (1994). "Megestrol acetate in patients with AIDS and cachexia." Ann Intern Med 121(6): 400-8.

Parker, Ba, et al.; Original Communication: Relation between food intake and visual analogue scale ratings of appetite and other sensations in healthy older and young subjects, European Journal of Clinical Nutrition 2004; 58:212-218.

Pascual Lopez, A., M. Roque i Figuls, et al. (2004). "Systematic review of megestrol acetate in the treatment of anorexia-cachexia syndrome." J Pain Symptom Manage 27(4): 360-9.

Pearson, William S., et al.; Treatment of HIV/AIDS in the Nursing Home: Variations in Rural and Urban Long-term Care Settings; Southern Medical Association 2004; 97(4):338-341.

Philpot, et al.; Weight Loss: A Vital Sign of Undernutrition in Long-Term Care; Annals of Long Term Care, available at www.LTCnutrition.org.

Piedrola, G. et al. Clinical features of adrenal insufficiency in patients with acquired immunodeficiency syndrome. Clinical Endocrinology (Oxford). Jul. 1996; 45(1):97-101.

Polsky, et al.; HIV—Associated Wasting in the HAART Era: Guidelines for Assessment, Diagnosis, and Treatment; Aids Patient Care and STDs 2001; 15(8):411-434.

Portenoy, R.K., et al.; The Memorial Symptom Assessment Scale: an Instrument for the Evaluation of Symptom Prevalence, Characteristics and Distress; European Journal of Cancer 1994; 30A(9):1326-1336.

Pourmotabbed, et al.; Endocrinology/Metabolism Development of Adrenal Insufficiency and Hypercalcemia after Discontinuation of Megestrol and Ketoconazole; p. 239A; Department of Medicine, University of Tennessee, Memphis, TN.

Quella, S. K., C. L. Loprinzi, et al. (1998). "Long term use of megestrol acetate by cancer survivors for the treatment of hot flashes." Cancer 82(9): 1784-8.

(56) References Cited

OTHER PUBLICATIONS

Raben, et al.; The reproducibility of subjective appetite scores; British Journal of Nutrition Apr. 1995; 73(4):517-530.
Raedler, T. J., H. Jahn, et al. (2003). "Acute effects of megestrol on the hypothalamic-pituitary-adrenal axis." Cancer Chemother Pharmacol 52(6): 482-6.
Rammohan, M. et al. Megestrol Acetate in a Moderate Dose for the treatment of malnutrition-inflammation complex in maintenance dialysis patients. J Renal Nutrition Jul. 2005; 1:154-158.
Raney; et al.; A Pilot Study to Assess the Use of Megesterol Acetate to Promote Weight Gain in Frail Elderly Persons Residing in Long-Term Care; JAMDA Jul./Aug. 2000; 1:154-158.
Ray, et al.; Antipsychotic and Antidepressant Drug Use in the Elderly and the Risk of Venous Thromboembolism; Thromb Haemost 2002; 88:205-209.
Reder, Elizabeth A. Keene; Health Resources and Services Administration Chapter 16, pp. 329-347.
Reuben, D. B., S. H. Hirsch, et al. (2005). "The effects of megestrol acetate suspension for elderly patients with reduced appetite after hospitalization: a phase II randomized clinical trial." J Am Geriatr Soc 53(6): 970-5.
Robetson, et al.; Geriatric Failure to Thrive; American Family Physician Jul. 15, 2004; 70(2):343-350.
Ron, I. G., V. Soyfer, et al. (2002). "A low-dose adrenocorticotropin test reveals impaired adrenal function in cancer patients receiving megestrol acetate therapy." Eur J Cancer 38(11): 1490-4.
Rosenberg, et al.; Cushing's Syndrome Induced by Megestrol Acetate in a Patient with AIDS; CID 1998; 27:217-218.
Rosenstein, David T., et al.; U.S. Department of Health and Human Services, Chapter 8, pp. 167-176.
Roubenoff, Ronenn; Acquired Immunodeficiency Syndrome Wasting, Functional Performance, and Quality of Life; The American Journal of Managed Care 2000; 6(9):1003-1016.
Rowland, K. M., Jr., C. L. Loprinzi, et al. (1996). "Randomized double-blind placebo-controlled trial of cisplatin and etoposide plus megestrol acetate/placebo in extensive-stage small-cell lung cancer: a North Central Cancer Treatment Group study." J Clin Oncol 14(1): 135-41.
Ruscin, J. M., R. L. Page, 2nd, et al. (2005). "Tumor necrosis factor-alpha and involuntary weight loss in elderly, community-dwelling adults." Pharmacotherapy 25(3): 313-9.
Ryan, et al.; Unintentional Weight Loss in Long-term Care: Predictor of Mortality in the Elderly; Southern Medical Journal 1995; 88(7):721-724.
Sacks, Gordon S., et al.; Use of Subjective Global Assessment to Identify Nutrition-Associated Complications and Death in Geriatric Long-Term Care Facility Residents, Journal of the American College of Nutrition 2000; 19(5):570-577.
Sandoval, et al.; Spiritual Care; Human Resources and Services Administration Chapter 13, pp. 289-299.
Sandoval, Rev. Carlos; Culture and Care; Health Resources and Services Administration Chapter 14, pp. 301-314.
Santos, et al.; Study of patients diagnosed with advanced HIV in the HAART era—OMEGA Cohort; International Journal of STD & AIDS 2005; 16:252-255.
Sarkisian, et al.; "Failure to Thrive" in Older Adults; Annals Internal Medicine 1996; 124:1072-1078.
Savient Pharmaceuticals, Inc. Oxandrin advertisements.
Schambelan, et al.; Recombinant Human Growth Hormone in Patients with HIV-Associated Wasting, A Randomized, Placebo-Controlled Trial; Annals of Internal Medicine 1996; 125(11):873-882.
Schmoll, E. (1992). "Risks and benefits of various therapies for cancer anorexia." Oncology 49 Suppl 2: 43-5.
Schmoll, E., H. Wilke, et al. (1991). "Megestrol acetate in cancer cachexia." Semin Oncol 18(1 Suppl 2): 32-4.
Schuster, M.D., Michael W., et al.; Progress Notes: Update on the Etiology and Treatment of Cancer-Associated Anorexia and Cachexia; HMP Communications, LLC, 2004, pp. 1-8.

Sellmeyer, D.E. and Grunfeld, C.; Endocrine and metabolic disturbances in human immunodeficiency virus infection and the acquired immune deficiency syndrome; Endocr. Rev. Oct. 1996; 17(5):518-532.
Selwyn, et al.; Overview of Clinical Issues; U.S. Department of Health and Human Services, Health Resources and Services Administration, HIV/AIDS Bureau Chapter 2, pp. 5-35.
Sharma, et al.; Cytokines, apoptosis and cachexia: the potential for TNF antagonism; International Journal of Cardiology 2002; 85:161-171.
Shields-Botella, J., I. Duc, et al. (2003). "An overview of nomegestrol acetate selective receptor binding and lack of estrogenic action on hormone-dependent cancer cells." J Steroid Biochem Mol Biol 87(2-3): 111-22.
Shikuma, et al.; HIV-Associated Wasting in the Era of Highly Active Antiretroviral Therapy: A Syndrome of Residue HIV Infection in Monocytes and Macrophages?; Clinical Infectious Diseases 2005; 40:1846-1848.
Silver, et al.; Nutritional Status in an Academic Nursing Home; the American Geriatrics Society 1988; 36:487-491.
Simmons, S. F. (2005). "The effect of megestrol acetate on oral food and fluid intake in nursing home residents: a pilot study." J Am Med Dir Assoc 6(3 Suppl): S4.
Simmons, S. F., K. A. Walker, et al. (2004). "The effect of megestrol acetate on oral food and fluid intake in nursing home residents: a pilot study." J Am Med Dir Assoc 5(1): 24-30.
Singhi, et. al.; Toxicity of Megestrol in Malnourished Chronic Dialysis Patients. Abstract A1079, Outcomes/Epidemiology/Clinical Trials.
Stockheim, J. A., J. J. Daaboul, et al. (1999). "Adrenal suppression in children with the human immunodeficiency virus treated with megestrol acetate." J Pediatr 134(3): 368-70.
Stolarczyk, R. et al. Twenty-four-hour urinary free cortisol in patients with acquired immunodeficiency syndrome. Metabolism. Jun. 1998; 47(6):690-4.
Subramanian, S., H. Goker, et al. (1997). "Clinical adrenal insufficiency in patients receiving megestrol therapy." Arch Intern Med 157(9): 1008-11.
Sullivan, et al.; Protein-Energy Undernutrition Among Elderly Hospitalized Patients a Prospective Study; JAMA 1999; 281(21):2013-2019.
Swan, et al.; Skilled Nursing Facility Care for Persons with AIDS: Comparison with Other Patients; American Journal of Public Health Mar. 1992, vol. 82 No. 3.
Tang, et al.; Weight Loss and Survival in HIV-Positive Patients in the Era of Highly Active Antiretroviral Therapy; Journal of Acquired Immune Deficiency Syndromes 2002, 31:230-236.
Tansan, S., Y. Koc, et al. (1997). "Augmentation of vincristine cytotoxicty by megestrol acetate." Cancer Chemother Pharmacol 39(4): 333-40.
Tchekmedyian, et al.; Cancer and AIDS Cachexia: Mechanisms and Approaches to Therapy; Oncology Supplement, Part II Nutrition in Patients with Cancer or AIDS 1993, pp. 55-59.
Tchekmedyian, N. S., M. Hickman, et al. (1992). "Megestrol acetate in cancer anorexia and weight loss." Cancer 69(5): 1268-74.
Tchekmedyian, N. S., N. Tait, et al. (1987). "High-dose megestrol acetate. A possible treatment for cachexia." Jama 257(9): 1195-8.
Testa, et al.; The Impact of AIDS—Associated Wasting on Quality of Life: Qualitative Issues of Measurement and Evaluation, J. Nutr. 1999; 129: 282S-289S.
Thomas, David R.; Progress Notes: Nutrition and Chronic Wounds; North American Center for Continuing Medical Education 2004; pp. 1-12.
Thomas, et al.; Incidence of venous thromboembolism in megestrol acetate users; JAMDA 2004; 5(1):65-66.
Thomas, et al.; Nutritional Considerations in Older People, Top Clin Chirop2002; :9(2):7-24.
Thomas, et al.; Regulation of Appetite in Older Adults; Annals of Long Term Care 2002; (Suppl) pp. 1-12.
Timpone, J. G., D. J. Wright, et al. (1997). "The safety and pharmacokinetics of single-agent and combination therapy with megestrol acetate and dronabinol for the treatment of HIV wasting syndrome. The DATRI 004 Study Group. Division of AIDS Treatment Research Initiative." AIDS Res Hum Retroviruses 13(4): 305-15.
Tisdale, Michael J.; Cancer Cachexia, Langenbecks Arch Surg. 2004; 389:299-305.

(56) References Cited

OTHER PUBLICATIONS

Turkoski, Beatrice B.; HIV and the Elderly Lovers, Home Healthcare Nurse 2002; 20(11):707-709.
Tuthill, Jean; Prevention of Skin Breakdown; Health Resources and Services Administration Chapter 25, pp. 505-514.
Vadell, et al.; Anticachectic efficacy of megestrol acetate at different doses and versus placebo in patients with neoplastic cachexia, Am J Clin Oncol 1998; 21(4):347-351.
Van Harken, D. R., J. C. Pei, et al. (1997). "Pharmacokinetic interaction of megestrol acetate with zidovudine in human immunodeficiency virus-infected patients." Antimicrob Agents Chemother 41(11): 2480-3.
Volicer, et al.; Effects of Dronabinol on Anorexia and Disturbed Behavior in Patients with Alzheimer's Disease; International Journal of Geriatric Psychiatry 1997; 12:913-919.
Von Roenn, J. H. (1994). "Randomized trials of megestrol acetate for AIDS-associated anorexia and cachexia." Oncology 51 Suppl 1: 19-24.
Von Roenn, J. H., D. Armstrong, et al. (1994). "Megestrol acetate in patients with AIDS-related cachexia." Ann Intern Med 121(6): 393-9.
Von Roenn, J. H., R. L. Murphy, et al. (1990). "Megestrol acetate for treatment of anorexia and cachexia associated with human immunodeficiency virus infection." Semin Oncol 17(6 Suppl 9): 13-6.
Wanke, Christine; Pathogenesis and Consequences of HIV-Associated Wasting; Acquir Immune Defic Syndr 2004; vol. 37, Supplement p. S277-S279.
Wanke, et al ; Collaborative Recommendations; The Approach to Diagnosis and Treatment of HIV Wasting; Acquir Immune Defi Syndr, 2004; 37(5):284-288.
Wanke, et al.; Guidelines for using Body Composition Measurement in Patients with Human Immunodeficiency Virus Infection; AIDS Patient Care and STDs 2002; 16:375-388.
Wanke, et al.; Unintentional Weight Loss: A Common Comorbidity and Strong Predictor of Morality in the Era of HAART; Clinical Infectious Disease 2000; 31(3):803-808.
Watson, Alguadia; HIV and the Elderly; The Riverside Program of Practical Nursing 2004, pp. 11-12.
Weikel, J. H., Jr., L. W. Nelson, et al. (1975). "A four-year evaluation of the chronic toxicity of megestrol acetate in dogs." Toxicol Appl Pharmacol 33(3): 414-26.
Weisberg, J., J. Wanger, et al. (2002). "Megestrol acetate stimulates weight gain and ventilation in underweight COPD patients." Chest 121(4): 1070-8.
Westhoff, et al.; Long Term Care Survey Reveals Challenges; Health Progress May 1993; pp. 38-42.
Westman, G., B. Bergman, et al. (1999). "Megestrol acetate in advanced, progressive, hormone-insensitive cancer. Effects on the quality of life: a placebo-controlled, randomised, multicentre trial." Eur J Cancer 35(4): 586-95.
Wheeler, et al.; Weight loss as a Predictor of Survival and Disease Progression in HIV Infection; Journal of Acquired Immune Deficiency Syndrome and Human Retro virology 1998; 18:80-85.
Wiedemann, K., M. Hirschmann, et al. (1998). "Sleep endocrine effects of megestrol acetate in healthy men." J Neuroendocrinol 10(9): 719-27.
Wilcox, et al.; AGA Technical Review: Malnutrition and Cachexia, Chronic Diarrhea, and Hepatobiliary Disease in Patients with Human Immunodeficiency Virus Infection; Gastroenterology 1996; 111:1724-52.
Willard, et al; Protein-Calorie Malnutrition in a Community Hospital; JAMA 1980; 249(17):1720-1722.
Willemse, P. H., L. D. Dikkeschei, et al. (1990). "Adrenal steroids as parameters of the bioavailability of MA and MPA." Eur J Cancer 26(3): 359-62.
Wilson, L.D. et al.; Anterior Putitiary and pituitary-dependent target organ function in men infected with the human immunodeficiency virus, Metabolism Jun. 1996; 45(6):738-46.
Wohlfeller, MD, Michael; U.S. Department of Health and Human Services, Chapter 7, pp. 157-165.
Wolff, F.H. et al. Low-dose adrenocorticotropin test in patients with the acquired immunodeficiency syndrome. Braz J Infect Dis. Apr. 2001; 5(2):53-9.
Wood, L., M. Palmer, et al. (1998). "Results of a phase III, double-blind, placebo-controlled trial of megestrol acetate modulation of P-glycoprotein-mediated drug resistance in the first-line management of small-cell lung carcinoma." Br J Cancer 77(4): 627-31.
Yeh, et al.; Geriatric Cachexia: the role of Cytokines; Am J Clin Nutr, American Society for Clinical Nutrition 1999; 70:183-97.
Yeh, et al.; The Correlation of Cytokine Levels with Body Weight After Megestrol Acetate Treatment in Geriatric Patients; Journal of Gerontology, Medical Sciences 2001; 56A(1):M48-54.
Yeh, S. S., A. Hafner, et al. (2004). "Risk factors relating blood markers of inflammation and nutritional status to survival in cachectic geriatric patients in a randomized clinical trial." J Am Geriatr Soc 52(10): 1708-12.
Yeh, S. S., S. Y. Wu, et al. (2000). "Improvement in quality-of-life measures and stimulation of weight gain after treatment with megestrol acetate oral suspension in geriatric cachexia: results of a double-bind, placebo-controlled study." J Am Geriatr Soc 48(5): 485-92.
Yeh, S. S., S. Y. Wu, et al. (2001). "The correlation of cytokine levels with body weight after megestrol acetate treatment in geriatric patients." J Gerontol A Biol Sci Med Sci 56(1): M48-54.
Yeh, S., S. Y. Wu, et al. (2000). "Quality of life and stimulation of weight gain after treatment with megestrol acetate: correlation between cytokine levels and nutritional stats, appetite in geriatric patients with wasting syndrome." J Nutr Health Aging 4(4): 246-51.
Buehler, Department of Health and Human Services, letter to Michelle Bonomi-Huvala, dated Aug. 19, 2005.
Bonomi-Huvala, Par Pharmaceutical, Inc., letter to Gary Buehler, dated Nov. 7, 2002.
Office Action from related U.S. Appl. No. 11/093,149 dated Feb. 17, 2009.
Food and Drug Administration-Guidance for Industry "Bioavailability and Bioequivalence Studies for Orally Administered Drug Products-General Considerations," Oct. 2000, 27 pages.
Office Action cited in related U.S. Appl. No. 10/420,927, dated Nov. 14, 2010.
Office Action cited in related U.S. Appl. No. 11/980,594, dated Aug. 20, 2009.
Office Action cited in related U.S. Appl. No. 11/979,253, dated Jul. 12, 2010.
Written Opinion from related Singapore Patent Application No. 2007188865-9, dated Oct. 6, 2009.
Physician's Desk Reference, 49 Ed., 1995, pp. 668-669.
Written Opinion from related Singapore Patent Application No. 2007188865-9, dated Dec. 19, 2008.
Office Action cited in related U.S. Appl. No. 11/093,149, dated May 4, 2012.
Office Action cited in related U.S. Appl. No. 12/826,557, dated Jun. 29, 2012.
Office Action cited in related U.S. Appl. No. 11/093,149, dated Sep. 20, 2012.
European Communication cited in related EP Patent Application No. 03724196.5 dated Aug. 5, 2011.
Office Action cited in related U.S. Appl. No. 12/826,557, dated Dec. 16, 2011.
Notice of Reasons for Rejection cited in related Japanese Patent Application No. 2008-518396, dated Feb. 8, 2012.
Office Action cited in related U.S. Appl. No. 10/420,927, dated Aug. 17, 2011.
Office Action issued in related U.S. Appl. No. 10/878,623, dated Nov. 5, 2014.

* cited by examiner

NANOPARTICULATE MEGESTROL FORMULATIONS

CROSS REFERENCE TO RELATED APPLICATIONS

This application is a continuation of U.S. patent application Ser. No. 10/878,623, filed Jun. 29, 2004, which is a continuation-in-part of U.S. patent application Ser. No. 10/412,669, filed Apr. 14, 2003, now U.S. Pat. No. 7,101,576, which claims the benefit of priority from U.S. Provisional Patent Application No. 60/371,680, filed Apr. 12, 2002, and U.S. Provisional Patent Application No. 60/430,348, filed Dec. 3, 2002. The contents of these applications are incorporated herein by reference in their entirety.

FIELD OF THE INVENTION

The present invention relates to a nanoparticulate composition comprising megestrol and preferably at least one surface stabilizer associated with the surface of the drug. The nanoparticulate megestrol particles have an effective average particle size of less than about 2000 nm.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent does not describe nanoparticulate compositions of megestrol.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive Nanoparticulate Compositions Having Cationic Surface Stabilizers;" U.S. Pat. No. 6,431,478 for "Small Scale Mill;" and U.S. Pat. No. 6,432,381 for "Methods for Targeting Drug Delivery to the Upper and/or Lower Gastrointestinal Tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding Megestrol

Megestrol acetate, also known as 17α-acetyloxy-6-methylpregna-4,6-diene-3,20-dione, is a synthetic progestin with progestational effects similar to those of progesterone. It is used in abortion, endometriosis, and menstrual disorders. It is also used in a variety of situations including treatment of breast cancer, contraception, and hormone replacement therapy in post-menopausal women. Megestrol acetate is also frequently prescribed as an appetite enhancer for patients in a wasting state, such as HIV wasting, cancer wasting, or anorexia. In combination with ethynyl estradiol it acts as an oral contraceptive. It is also administered to subjects after castration.

Megestrol acetate is marketed by Par Pharmaceuticals, Inc. and under the brand name Megace® by Bristol Myers Squibb Co. Typical commercial formulations are relatively large volume. For example, Par Pharmaceuticals, Inc. megestrol acetate oral suspension contains 40 mg of micronized megestrol acetate per ml, and the package insert recommends an initial adult dosage of megestrol acetate oral suspension of 800 mg/day (20 mL/day). The commercial formulations of megestrol acetate are highly viscous suspensions, which have a relatively long residence time in the mouth and any tubing. Highly viscous substances are not well accepted by patient populations, particularly patients suffering wasting and those that are intubated.

U.S. Pat. No. 6,028,065 for "Flocculated Suspension of Megestrol Acetate," assigned to Pharmaceutical Resources, Inc. (Spring Valley, N.Y.), describes oral pharmaceutical micronized megestrol acetate compositions in the form of a stable flocculated suspension in water. The compositions comprise at least one compound selected from the group consisting of polyethylene glycol, propylene glycol, glycerol, and sorbitol; and a surfactant, wherein polysorbate and polyethylene glycol are not simultaneously present. U.S. Pat. No. 6,268,356, also for "Flocculated Suspension of Megestrol Acetate," and assigned to Pharmaceutical Resources, Inc., describes methods of treating a neoplastic condition comprising administering the composition of U.S. Pat. No. 6,028,065.

Another company that has developed a megestrol formulation is Eurand (Milan, Italy). Eurand's formulation is a modified form of megestrol acetate having increased bioavailability. Eurand structurally modifies poorly soluble drugs to increase their bioavailability. See www.eurand.com. For megestrol acetate, Eurand uses its' "Biorise" process, in which a New Physical Entity (NPE) is created by physically breaking down megestrol's crystal lattice. This results in drug nanocrystals and/or amorphous drug, which are then stabilized with biologically inert carriers. Eurand uses three types of carriers: swellable microparticles, composite swellable microparticles, and cyclodextrins. See e.g., http://www.eurand.com/page.php?id=39. Such a delivery system can be undesirable, as "breaking down" an active agent's crystalline structure can modify the activity of the active agent. A drug delivery system which does not alter the structure of the active agent is preferable.

Among the progestins, megestrol acetate is one of the few that can be administered orally because of its reduced first-pass (hepatic) metabolism, compared to the parent hormone. In addition, it is claimed to be superior to 19-nor compounds as an antifertility agent because it has less effect on the endometrium and vagina. See *Stedman's Medical Dictionary*, 25$^{th}$ Ed., page 935 (Williams & Wilkins, MD 1990).

There is a need in the art for megestrol formulations which exhibit increased bioavailability, less variability, and/or less viscosity as compared to conventional microparticulate megestrol formulations. The present invention satisfies these needs.

SUMMARY OF THE INVENTION

The invention relates to nanoparticulate megestrol compositions. The compositions comprise megestrol and preferably at least one surface stabilizer associated with the surface of the megestrol particles. The nanoparticulate megestrol particles have an effective average particle size of less than about 2000 nm.

Another aspect of the invention is directed to pharmaceutical compositions comprising a nanoparticulate megestrol composition of the invention. The pharmaceutical compositions preferably comprise megestrol, at least one surface stabilizer, and a pharmaceutically acceptable carrier, as well as any desired excipients.

This invention further discloses a method of making a nanoparticulate megestrol composition according to the invention. Such a method comprises contacting megestrol particles and at least one surface stabilizer for a time and under conditions sufficient to provide a nanoparticulate megestrol composition. The one or more surface stabilizers can be contacted with megestrol either before, during, or after size reduction of the megestrol.

The present invention is also directed to methods of treatment using the nanoparticulate compositions of the invention for conditions such as endometriosis, dysmenorrhea, hirsutism, uterine bleeding, neoplastic diseases, methods of appetite enhancement, contraception, hormone replacement therapy, and treating patients following castration. Such methods comprises administering to a subject a therapeutically effective amount of a nanoparticulate megestrol composition according to the invention.

Finally, the present invention is directed to megestrol acetate compositions with improved physical (viscosity) and pharmacokinetic profiles (such as less variability) over traditional forms of megestrol acetate.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1:
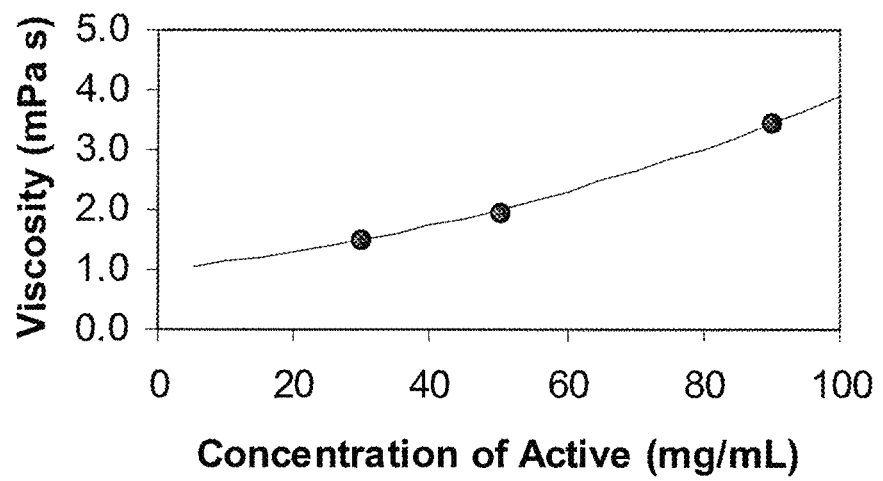
FIG. 1: Illustrates viscosity in units of mPa s as a function of concentration. Circles indicate the experimental values and the line illustrates the expected trend.

The present invention is directed to nanoparticulate compositions comprising megestrol particles having an effective average particle size of less than about 2 microns. The compositions comprise megestrol and preferably at least one surface stabilizer associated with the surface of the drug.

As taught in the '684 patent, not every combination of surface stabilizer and active agent will result in a stable nanoparticulate composition. It was surprisingly discovered that stable nanoparticulate megestrol compositions can be made.

For example, nanoparticulate megestrol compositions with hydroxypropyl methylcellulose (HPMC) and sodium lauryl sulfate (SLS) as surface stabilizers remained stable in an electrolyte solution mimicking the physiological pH of the stomach. Nanoparticulate megestrol compositions comprising HPMC and SLS are stable for several weeks at temperatures up to 40° C. with only minimal particle size growth. In addition, nanoparticulate megestrol compositions with hydroxypropylcellulose (HPC) and dioctyl sodium sulfosuccinate (DOSS) as surface stabilizers, HPMC and DOSS as surface stabilizers, polyvinylpyrrolidone (PVP) and DOSS as surface stabilizers, and Plasdone® S630 and DOSS as surface stabilizers were stable in electrolyte fluids and exhibited acceptable physical stability at 5° C. for 4 weeks. (Plasdone® S630 (ISP) is a random copolymer of vinyl acetate and vinyl pyrrolidone.) Moreover, the nanoparticulate megestrol/HPMC/SLS and nanoparticulate megestrol/HPMC/DOSS compositions also exhibited acceptable physical stability at 25° C. and 40° C. for 4 weeks.

Advantages of the nanoparticulate megestrol compositions of the invention include, but are not limited to: (1) low viscosity liquid nanoparticulate megestrol dosage forms; (2) for liquid nanoparticulate megestrol compositions having a low viscosity—better subject compliance due to the perception of a lighter formulation which is easier to consume and digest; (3) for liquid nanoparticulate megestrol compositions having a low viscosity—ease of dispensing because one can use a cup or a syringe; (4) faster onset of action; (5) smaller doses of megestrol required to obtain the same pharmacological effect as compared to conventional microcrystalline forms of megestrol; (6) increased bioavailability as compared to conventional microcrystalline forms of megestrol; (7) substantially similar pharmacokinetic profiles of the nanoparticulate megestrol compositions when administered in the fed versus the fasted state; (8) bioequivalency of the nanoparticulate megestrol compositions when administered in the fed versus the fasted state; (9) redispersibility of the nanoparticulate megestrol particles present in the compositions of the invention following administration; (10) bioadhesive nanoparticulate megestrol compositions; (11) improved pharmacokinetic profiles, such as more rapid megestrol absorption, greater megestrol absorption, and longer megestrol dose retention in the blood following administration; (12) the nanoparticulate megestrol compositions can be used in conjunction with other active agents; (13) the nanoparticulate megestrol compositions preferably exhibit an increased rate of dissolution as compared to conventional microcrystalline forms of megestrol; (14) improved performance characteristics for oral, intravenous, subcutaneous, or intramuscular injection, such as higher dose loading and smaller tablet or liquid dose volumes; (15) the nanoparticulate megestrol compositions are suitable for parenteral administration; (16) the nanoparticulate megestrol compositions can be sterile filtered; and (17) the nanoparticulate megestrol compositions do not require organic solvents or pH extremes.

The present invention is described herein using several definitions, as set forth below and throughout the application.

"About" will be understood by persons of ordinary skill in the art and will vary to some extent on the context in which the term is used. If there are uses of the term which are not clear to persons of ordinary skill in the art given the context in which it is used, "about" will mean up to plus or minus 10% of the particular term.

As used herein with reference to stable drug particles, "stable" means that the megestrol particles do not appreciably flocculate or agglomerate due to interparticle attractive forces or otherwise increase in particle size.

"Conventional active agents or drugs" refers to non-nanoparticulate compositions of active agents or solubilized active agents or drugs. Non-nanoparticulate active agents have an effective average particle size of greater than about 2 microns.

A. Preferred Characteristics of the Nanoparticulate Megestrol Compositions of the Invention 1. Low Viscosity Typical commercial formulations of megestrol, such as Megace®, are relatively large volume, highly viscous substances that are not well accepted by patient populations, particularly subjects suffering from wasting. "Wasting" is a condition in which a subject finds it difficult to eat because, for example, food makes the subject nauseous. A highly viscous medicine is not compatible with treating such a condition, as frequently the highly viscous substance can cause additional nausea.

Moreover, viscous solutions can be problematic in parenteral administration because these solutions require a slow syringe push and can stick to tubing. In addition, conventional formulations of poorly water-soluble active agents, such as megestrol, tend to be unsafe for intravenous administration techniques, which are used primarily in conjunction with highly water-soluble substances.

Liquid dosage forms of the nanoparticulate megestrol compositions of the invention provide significant advantages over conventional liquid megestrol dosage forms. The low viscosity and silky texture of liquid dosage forms of the nanoparticulate megestrol compositions of the invention results in advantages in both preparation and use. These advantages include, for example: (1) better subject compliance due to the perception of a lighter formulation which is easier to consume and digest; (2) ease of dispensing because one can use a cup or a syringe; (3) potential for formulating a higher concentration of megestrol resulting in a smaller dosage volume and thus less volume for the subject to consume; and (4) easier overall formulation concerns.

Liquid megestrol dosage forms which are easier to consume are especially important when considering juvenile patients, terminally ill patients, and patients suffering from gastrointestinal tract dysfunction or other conditions where nausea and vomiting are symptoms. For example, patients suffering from cancer or AIDS-related complications are commonly hypermetabolic and, at various stages of disease, exhibit gastrointestinal dysfunction. Additionally, drugs used to treat these conditions often cause nausea and vomiting. Viscous or gritty formulations, and those that require a relatively large dosage volume, are not well tolerated by patient populations suffering from wasting associated with these diseases because the formulations can exacerbate nausea and encourage vomiting.

The viscosities of liquid dosage forms of nanoparticulate megestrol according to the invention are preferably less than about 1/200, less than about 1/175, less than about 1/150, less than about 1/125, less than about 1/100, less than about 1/75, less than about 1/50, or less than about 1/25 of existing commercial liquid oral megestrol acetate compositions, e.g. Megace®, at about the same concentration per ml of megestrol.

Typically the viscosity of liquid nanoparticulate megestrol dosage forms of the invention is from about 175 mPa s to about 1 mPa s, from about 150 mPa s to about 1 mPa, from about 125 mPa s to about 1 mPa s, from about 100 mPa s to about 1 mPa s, from about 75 mPa s to about 1 mPa s, from about 50 mPa s to about 1 mPa s, from about 25 mPa s to about 1 mPa s, from about 15 mPa s to about 1 mPa s, or from about 5 mPa s to about 1 mPa s. Such a viscosity is much more attractive for subject consumption and may lead to better overall subject compliance.

Viscosity is concentration and temperature dependent. Typically, a higher concentration results in a higher viscosity, while a higher temperature results in a lower viscosity. Viscosity as defined above refers to measurements taken at about 20° C. (The viscosity of water at 20° C. is 1 mPa s.) The invention encompasses equivalent viscosities measured at different temperatures.

A viscosity of 1.5 mPa s for a nanoparticulate megestrol dispersion having a concentration of 30 mg/mL, measured at 20° C., was obtained by the inventors. An equivalent viscosity at 4% active agent concentration would be 1.7 mPa s. Higher and lower viscosities can be obtained by varying the temperature and concentration of megestrol.

Another important aspect of the invention is that the nanoparticulate megestrol compositions of the invention are not turbid. "Turbid," as used herein refers to the property of particulate matter that can be seen with the naked eye or that which can be felt as "gritty." The nanoparticulate megestrol compositions of the invention can be poured out of or extracted from a container as easily as water, whereas a conventional standard commercial (i.e., non-nanoparticulate or solubilized) megestrol liquid dosage form exhibits notably more "sluggish" characteristics.

The liquid formulations of this invention can be formulated for dosages in any volume but preferably equivalent or smaller volumes than existing commercial formulations.

2. Fast Onset of Activity

The use of conventional formulations of megestrol is not ideal due to delayed onset of action. In contrast, the nanoparticulate megestrol compositions of the invention exhibit faster therapeutic effects.

Preferably, following administration the nanoparticulate megestrol compositions of the invention have a $T_{max}$ of less than about 5 hours, less than about 4.5 hours, less than about 4 hours, less than about 3.5 hours, less than about 3 hours, less than about 2.75 hours, less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, or less than about 10 minutes.

3. Increased Bioavailability

The nanoparticulate megestrol compositions of the invention preferably exhibit increased bioavailability and require smaller doses as compared to prior conventional megestrol compositions administered at the same dose.

Any drug, including megestrol, can have adverse side effects. Thus, lower doses of megestrol which can achieve the same or better therapeutic effects as those observed with larger doses of conventional megestrol compositions are desired. Such lower doses can be realized with the nanoparticulate megestrol compositions of the invention because the greater bioavailability observed with the nanoparticulate megestrol compositions as compared to conventional drug formulations means that smaller doses of drug are required to obtain the desired therapeutic effect. Specifically, a once a day dose of about 375 mg/5 mL (75 mg/mL) of a nanoparticulate megestrol acetate composition is considered equivalent to an 800 mg dose of Megace®.

Administration of nanoparticulate megestrol formulations of the present invention can exhibit bioavailability, as determined by AUC0-t, in an amount of about 3000 ng hr/ml to about 15,000 ng hr/ml, wherein Cmax is about 300 ng/ml to about 1400 ng/ml, 1500 ng/ml, 1600 ng/ml, 1645 ng/ml or 1700 ng/ml in a fed human subject and AUC0-t in an amount of about 2000 ng hr/ml to about 9000 ng hr/ml, wherein Cmax is about 300 ng/ml to about 2000 ng/ml in a fasted human subject. Preferably, nanoparticulate megestrol formulations of the present invention exhibit comparable bioavailability in a range of between about 75 and about 130%, more preferably between about 80% and about 125%, of the specified therapeutic parameter (e.g., AUC0-t or Cmax).

4. The Pharmacokinetic Profiles of the Nanoparticulate Megestrol Compositions of the Invention are not Substantially Affected by the Fed or Fasted State of the Subject Ingesting the Compositions The invention encompasses nanoparticulate megestrol compositions wherein the pharmacokinetic profile of the megestrol is not substantially affected by the fed or fasted state of a subject ingesting the composition. This means that there is no substantial difference in the quantity of megestrol absorbed or the rate of megestrol absorption when the nanoparticulate megestrol compositions are administered in the fed versus the fasted state. Thus, the invention encompasses nanoparticulate megestrol compositions that can substantially eliminate the effect of food on the pharmacokinetics of megestrol.

The difference in absorption of the nanoparticulate megestrol composition of the invention, when administered in the fed versus the fasted state, is less than about 35%, less than about 30%, less than about 25%, less than about 20%, less than about 15%, less than about 10%, less than about 5%, or less than about 3%. This is an especially important feature in treating patients with difficulty in maintaining a fed state.

In addition, preferably the difference in the rate of absorption (i.e., $T_{max}$) of the nanoparticulate megestrol compositions of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference.

Benefits of a dosage form which substantially eliminates the effect of food include an increase in subject convenience, thereby increasing subject compliance, as the subject does not need to ensure that they are taking a dose either with or without food.

5. Redispersibility Profiles of the Nanoparticulate Megestrol Compositions of the Invention An additional feature of the nanoparticulate megestrol compositions of the invention is that the compositions redisperse such that the effective average particle size of the redispersed megestrol particles is less than about 2 microns. This is significant, as if upon administration the nanoparticulate megestrol particles present in the compositions of the invention did not redisperse to a substantially nanoparticulate particle size, then the dosage form may lose the benefits afforded by formulating megestrol into a nanoparticulate particle size.

This is because nanoparticulate megestrol compositions benefit from the small particle size of megestrol; if the nanoparticulate megestrol particles do not redisperse into the small particle sizes upon administration, then "clumps" or agglomerated megestrol particles are formed. With the formation of such agglomerated particles, the bioavailability of the dosage form may fall.

Preferably, the redispersed megestrol particles of the invention have an effective average particle size, by weight, of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Moreover, the nanoparticulate megestrol compositions of the invention exhibit dramatic redispersion of the nanoparticulate megestrol particles upon administration to a mammal, such as a human or animal, as demonstrated by reconstitution in a biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

6. Bioadhesive Nanoparticulate Megestrol Compositions

Bioadhesive nanoparticulate megestrol compositions of the invention comprise at least one cationic surface stabilizer, which are described in more detail below. Bioadhesive formulations of megestrol exhibit exceptional bioadhesion to biological surfaces, such as mucous.

In the case of bioadhesive nanoparticulate megestrol compositions, the term "bioadhesion" is used to describe the adhesion between the nanoparticulate megestrol compositions and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

The bioadhesive megestrol compositions of the invention are useful in any situation in which it is desirable to apply the compositions to a biological surface. The bioadhesive megestrol compositions coat the targeted surface in a continuous and uniform film which is invisible to the naked human eye.

A bioadhesive nanoparticulate megestrol composition slows the transit of the composition, and some megestrol particles would also most likely adhere to tissue other than the mucous cells and therefore give a prolonged exposure to megestrol, thereby increasing absorption and the bioavailability of the administered dosage.

7. Pharmacokinetic Profiles of the Nanoparticulate Megestrol Compositions of the Invention The present invention also provides compositions of nanoparticulate megestrol having a desirable pharmacokinetic profile when administered to mammalian subjects. The desirable pharmacokinetic profile of the nanoparticulate megestrol compositions comprise the parameters: (1) that the $T_{max}$ of megestrol, when assayed in the plasma of the mammalian subject, is less than about 5 hours; and (2) a $C_{max}$ of megestrol is greater than about 30 ng/ml. Preferably, the $T_{max}$ parameter of the pharmacokinetic profile is not greater than about 3 hours. Most preferably, the $T_{max}$ parameter of the pharmacokinetic profile is not greater than about 2 hours.

The desirable pharmacokinetic profile, as used herein, is the pharmacokinetic profile measured after the initial dose of megestrol. For example, in a subject receiving 40 mg of megestrol four times a day, the $T_{max}$ and $C_{max}$ after the initial dose must be less than about 5 hours and greater than about 30 ng/ml, respectively. The compositions can be formulated in any way as described below.

Current formulations of megestrol include oral suspensions and tablets. According to the package insert of Megace®, the pharmacokinetic profile of the oral suspension contains parameters such that the median $T_{max}$ is 5 hours and the mean $C_{max}$ is 753 ng/ml. Further, the $T_{max}$ and $C_{max}$ for the Megace® 40 mg tablet, after the initial dose, is 2.2 hours and 27.6 ng/ml, respectively. *Physicians Desk Reference, 55th* Ed., 2001. The nanoparticulate megestrol compositions of the invention simultaneously improve upon at least the $T_{max}$ and $C_{max}$ parameters of the pharmacokinetic profile of megestrol.

In one embodiment, a threshold blood plasma concentration of megestrol of about 700 ng/ml is attained in less than about 5 hours after administration of the formulation, and preferably not greater than about 3 hours.

Preferably, the $T_{max}$ of an administered dose of a nanoparticulate megestrol composition is less than that of a conventional standard commercial non-nanoparticulate megestrol composition, administered at the same dosage. In addition, preferably the $C_{max}$ of a nanoparticulate megestrol composition is greater than the $C_{max}$ of a conventional standard commercial non-nanoparticulate megestrol composition, administered at the same dosage.

A preferred nanoparticulate megestrol composition of the invention exhibits in comparative pharmacokinetic testing with a standard commercial formulation of megestrol, such as Megace® oral suspension or tablet from Bristol Myers Squibb, a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the standard commercial formulation of megestrol.

A preferred nanoparticulate megestrol composition of the invention exhibits in comparative pharmacokinetic testing with a standard commercial formulation of megestrol, such as Megace® oral suspension or tablet from Bristol Myers Squibb, a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 200%, greater than about 500% or greater than about 800% than the $C_{max}$ exhibited by the standard commercial formulation of megestrol.

There is no critical upper limit of blood plasma concentration so long as the dosage amounts set out below are not significantly exceeded. A suitable dose of megestrol, administered according to the method of the invention, is typically in the range of about 1 mg/day to about 1000 mg/day, or from about 40 mg/day to about 800 mg/day. In one embodiment, a nanoparticulate megestrol composition is administered at a dose of 575 mg/day. In other embodiments, the nanoparticulate megestrol composition is administered at doses of 625 mg/day or 675 mg/day. Preferably, the therapeutically effective amount of the nanoparticulate megestrol compositions of the invention is about ⅙, ⅕, ¼, ⅓, ½, ⅔, ¾ or ⅚ of the therapeutically effective amount of existing commercial megestrol formulations.

Any standard pharmacokinetic protocol can be used to determine blood plasma concentration profile in humans following administration of a nanoparticulate megestrol composition, and thereby establish whether that composition meets the pharmacokinetic criteria set out herein. For example, a randomized single-dose crossover study can be performed using a group of healthy adult human subjects. The number of subjects should be sufficient to provide adequate control of variation in a statistical analysis, and is typically about 10 or greater, although for certain purposes a smaller group can suffice. Each subject receives by oral administration at time zero a single dose (e.g., 300 mg) of a test formulation of megestrol, normally at around 8 am following an overnight fast. The subjects continue to fast and remain in an upright position for about 4 hours after administration of the megestrol formulation. Blood samples are collected from each subject prior to administration (e.g., 15 minutes) and at several intervals after administration. For the present purpose it is preferred to take several samples within the first hour, and to sample less frequently thereafter. Illustratively, blood samples could be collected at 15, 30, 45, 60, and 90 minutes after administration, then every hour from 2 to 10 hours after administration. Additional blood samples may also be taken later, for example at 12 and 24 hours after administration. If the same subjects are to be used for study of a second test formulation, a period of at least 7 days should elapse before administration of the second formulation. Plasma is separated from the blood samples by centrifugation and the separated plasma is analyzed for megestrol by a validated high performance liquid chromatography (HPLC) procedure, such as for example Garver et al., *J. Pharm. Sci.* 74(6):664-667 (1985), the entirety of which is hereby incorporated by reference. Plasma concentrations of megestrol referenced herein are intended to mean total megestrol concentrations including both free and bound megestrol.

Any formulation giving the desired pharmacokinetic profile is suitable for administration according to the present methods. Exemplary types of formulations giving such profiles are liquid dispersions and solid dose forms of nanoparticulate megestrol. Dispersions of megestrol have proven to be stable at temperatures up to 50° C. If the liquid dispersion medium is one in which the nanoparticulate megestrol has very low solubility, the nanoparticulate megestrol particles are present as suspended particles. The smaller the megestrol particles, the higher the probability that the formulation will exhibit the desired pharmacokinetic profile.

8. Combination Pharmacokinetic Profile Compositions

In yet another embodiment of the invention, a first nanoparticulate megestrol composition providing a desired pharmacokinetic profile is co-administered, sequentially administered, or combined with at least one other megestrol composition that generates a desired different pharmacokinetic profile. More than two megestrol compositions can be co-administered, sequentially administered, or combined. While the first megestrol composition has a nanoparticulate particle size, the additional one or more megestrol compositions can be nanoparticulate, solubilized, or have a conventional microparticulate particle size.

For example, a first megestrol composition can have a nanoparticulate particle size, conferring a short $T_{max}$ and typically a higher $C_{max}$. This first megestrol composition can be combined, co-administered, or sequentially administered with a second composition comprising: (1) megestrol having a larger (but still nanoparticulate as defined herein) particle size, and therefore exhibiting slower absorption, a longer $T_{max}$, and typically a lower $C_{max}$; or (2) a microparticulate or solubilized megestrol composition, exhibiting a longer $T_{max}$, and typically a lower $C_{max}$.

The second, third, fourth, etc., megestrol compositions can differ from the first, and from each other, for example: (1) in the effective average particle sizes of megestrol; or (2) in the dosage of megestrol. Such a combination composition can reduce the dose frequency required.

If the second megestrol composition has a nanoparticulate particle size, then preferably the megestrol particles of the second composition have at least one surface stabilizer associated with the surface of the drug particles. The one or more surface stabilizers can be the same as or different from the surface stabilizer(s) present in the first megestrol composition.

Preferably where co-administration of a "fast-acting" formulation and a "longer-lasting" formulation is desired, the two formulations are combined within a single composition, for example a dual-release composition.

9. Combination Active Agent Compositions

The invention encompasses the nanoparticulate megestrol compositions of the invention formulated or co-administered with one or more non-megestrol active agents, which are either conventional (solubilized or microparticulate) or nanoparticulate. Methods of using such combination compositions are also encompassed by the invention. The non-megestrol active agents can be present in a crystalline phase, an amorphous phase, a semi-crystalline phase, a semi-amorphous phase, or a mixture thereof.

The compound to be administered in combination with a nanoparticulate megestrol composition of the invention can be formulated separately from the nanoparticulate megestrol composition or co-formulated with the nanoparticulate megestrol composition. Where a nanoparticulate megestrol composition is co-formulated with a second active agent, the second active agent can be formulated in any suitable manner, such as immediate-release, rapid-onset, sustained-release, or dual-release form.

If the non-megestrol active agent has a nanoparticulate particle size i.e., a particle size of less than about 2 microns, then preferably it will have one or more surface stabilizers associated with the surface of the active agent. In addition, if the active agent has a nanoparticulate particle size, then it is preferably poorly soluble and dispersible in at least one liquid dispersion media. By "poorly soluble" it is meant that the active agent has a solubility in a liquid dispersion media of less than about 30 mg/mL, less than about 20 mg/mL, less than about 10 mg/mL, or less than about 1 mg/mL. Useful liquid dispersion medias include, but are not limited to, water, aqueous salt solutions, safflower oil, and solvents such as ethanol, t-butanol, hexane, and glycol.

Such non-megestrol active agents can be, for example, a therapeutic agent. A therapeutic agent can be a pharmaceutical agent, including biologics. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's *The Extra Pharmacopoeia*, 31*st* Edition (The Pharmaceutical Press, London, 1996), specifically incorporated by reference. The active agents are commercially available and/or can be prepared by techniques known in the art.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. Dietary supplements and nutraceuticals are also disclosed in *Physicians' Desk Reference for Nutritional Supplements*, 1st Ed. (2001) and *The Physicians' Desk Reference for Herbal Medicines*, 1st Ed. (2001), both of which are also incorporated by reference. A nutraceutical or dietary supplement, also known as a phytochemical or functional food, is generally any one of a class of dietary supplements, vitamins, minerals, herbs, or healing foods that have medical or pharmaceutical effects on the body.

Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., arginine, iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bioengineered foods genetically engineered to have a desired property, also known as "pharmafoods."

10. Sterile Filtered Nanoparticulate Megestrol Compositions

The nanoparticulate megestrol compositions of the invention can be sterile filtered. This obviates the need for heat sterilization, which can harm or degrade megestrol, as well as result in crystal growth and particle aggregation.

Sterile filtration can be difficult because of the required small particle size of the composition. Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize conventional suspensions of micron-sized megestrol because the megestrol particles are too large to pass through the membrane pores.

A sterile nanoparticulate megestrol dosage form is particularly useful in treating immunocompromised patients, infants or juvenile patients, and the elderly, as these patient groups are the most susceptible to infection caused by a non-sterile liquid dosage form.

Because the nanoparticulate megestrol compositions of the invention can be sterile filtered, and because the compositions can have a very small megestrol effective average particle size, the compositions are suitable for parenteral administration.

11. Miscellaneous Benefits of the Nanoparticulate Megestrol Compositions of the Invention The nanoparticulate megestrol compositions preferably exhibit an increased rate of dissolution as compared to conventional microcrystalline forms of megestrol. In addition, the compositions of the invention exhibit improved performance characteristics for oral, intravenous, subcutaneous, or intramuscular injection, such as higher dose loading and smaller tablet or liquid dose volumes. Moreover, the nanoparticulate megestrol compositions of the invention do not require organic solvents or pH extremes.

Another benefit of the nanoparticulate megestrol compositions of the invention is that is was surprisingly discovered that upon administration, nanoparticulate compositions of megestrol acetate reach therapeutic blood levels within one dose. This is in dramatic contrast to the current commercially available megestrol acetate composition (Megace® by Bristol Myers Squibb Co.), which requires multiple doses, administered over several days to a week, to build up to a therapeutic level of drug in the blood stream.

B. Compositions

The invention provides compositions comprising nanoparticulate megestrol particles and preferably at least one surface stabilizer. The one or more surface stabilizers are preferably associated with the surface of the megestrol particles. Surface stabilizers useful herein preferably do not chemically react with the megestrol particles or itself. Individual molecules of the surface stabilizer are essentially free of intermolecular cross-linkages.

The present invention also includes nanoparticulate megestrol compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

1. Megestrol Particles

As used herein the term megestrol, which is the active ingredient in the composition, is used to mean megestrol, megestrol acetate (17α-acetyloxy-6-methylpregna-4,6-diene-3,20-dione), or a salt thereof. The megestrol particles can be present in a crystalline phase, an amorphous phase, a semi-crystalline phase, a semi-amorphous phase, or a mixture thereof.

Megestrol acetate is well known in the art and is readily recognized by one of ordinary skill. Generally, megestrol is used for treating breast cancer, endometrial cancer and, less frequently, prostate cancer. Megestrol is also frequently used as an appetite stimulant for patients in a wasting state, such as HIV wasting, cancer wasting, and anorexia. Megestrol may be used for other indications where progestins are typically used, such as hormone replacement therapy in post-menopausal women and oral contraception. Further, megestrol may be used for ovarian suppression in several conditions such as endometriosis, hirsutism, dysmenorrhea, and uterine bleeding, as well as uterine cancer, cervical cancer, and renal cancer. Megestrol is also used in patients following castration.

2. Surface Stabilizers

The choice of a surface stabilizer for megestrol is non-trivial. Accordingly, the present invention is directed to the surprising discovery that nanoparticulate megestrol compositions can be made.

Combinations of more than one surface stabilizer can be used in the invention. Preferred surface stabilizers include, but are not limited to, hydroxypropyl methylcellulose, hydroxypropylcellulose, polyvinylpyrrolidone, random copolymers of vinyl pyrrolidone and vinyl acetate, sodium lauryl sulfate, dioctylsulfosuccinate or a combination thereof. Preferred primary surface stabilizers include, but are not limited to, hydroxypropyl methylcellulose, hydroxypropylcellulose, polyvinylpyrrolidone, random copolymers of vinyl pyrrolidone and vinyl acetate, or a combination thereof. Preferred secondary surface stabilizers include, but are not limited to, sodium lauryl sulfate and dioctylsulfosuccinate.

Other surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, cationic, ionic, and zwitterionic surfactants.

Representative examples of surface stabilizers include hydroxypropyl methylcellulose, hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508®(T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}, C_{15}, C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Distearyldimonium chloride), cetyl pyridinium bromide or chloride, halide salts of quaternized polyoxyethylalkyamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

3. Other Pharmaceutical Excipients

Pharmaceutical megestrol compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Megestrol or Active Agent Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise nanoparticulate megestrol particles which have an effective average particle size of less than about 2000 nm (i.e., 2 microns). In other embodiments of the invention, the megestrol particles have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, when measured by the above techniques.

If the nanoparticulate megestrol composition additionally comprises one or more non-megestrol nanoparticulate active agents, then such active agents have an effective average particle size of less than about 2000 nm (i.e., 2 microns). In other embodiments of the invention, the nanoparticulate non-megestrol active agents can have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the nanoparticulate megestrol or nanoparticulate non-megestrol active agent particles have a particle size of less than about 2000 nm, by weight, when measured by the above-noted techniques. Preferably, at least about 70%, about 90%, about 95%, or about 99% of the nanoparticulate megestrol or nanoparticulate non-megestrol active agent particles have a particle size of less than the effective average, i.e., less than about 2000 nm, less than about 1900 nm, less than about 1800 nm, etc.

If the nanoparticulate megestrol composition is combined with a conventional or microparticulate megestrol composition or non-megestrol active agent composition, then such a composition is either solubilized or has an effective average particle size of greater than about 2 microns. By "an effective average particle size of greater than about 2 microns" it is meant that at least 50% of the conventional megestrol or non-megestrol active agent particles have a particle size of greater than about 2 microns, by weight, when measured by the above-noted techniques. In other embodiments of the invention, at least about 70%, about 90%, about 95%, or about 99% of the conventional megestrol or non-megestrol active agent particles have a particle size greater than about 2 microns.

5. Concentration of Nanoparticulate Megestrol and Surface Stabilizers

The relative amounts of nanoparticulate megestrol and one or more surface stabilizers can vary widely. The optimal amount of the individual components can depend, for example, the hydrophilic lipophilic balance (HLB), melting point, and the surface tension of water solutions of the stabilizer, etc.

The concentration of megestrol can vary from about 99.5% to about 0.001%, from about 95% to about 0.1%, or from about 90% to about 0.5%, by weight, based on the total combined dry weight of the megestrol and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the megestrol and at least one surface stabilizer, not including other excipients.

If a combination of two or more surface stabilizers is employed in the composition, the concentration of the at least one primary surface stabilizer can vary from about 0.01% to about 99.5%, from about 0.1% to about 95%, or from about 0.5% to about 90%, by weight, based on the total combined dry weight of the megestrol, at least one primary surface stabilizer, and at least one secondary surface stabilizer, not including other excipients. In addition, the concentration of the at least one secondary surface stabilizer can vary from about 0.01% to about 99.5%, from about 0.1% to about 95%, or from about 0.5% to about 90%, by weight, based on the total combined dry weight of the megestrol, at least one primary surface stabilizer, and at least one secondary surface stabilizer, not including other excipients.

C. Methods of Making Nanoparticulate Megestrol Compositions

The nanoparticulate megestrol compositions can be made using, for example, milling, homogenization, or precipitation techniques. Exemplary methods of making nanoparticulate compositions are described in the '684 patent.

Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate megestrol compositions can be utilized in solid or liquid dosage formulations, such as controlled release formulations, solid dose fast melt formulations, aerosol formulations, lyophilized formulations, tablets, capsules, etc.

1. Milling to Obtain Nanoparticulate Megestrol Dispersions

Milling megestrol to obtain a nanoparticulate megestrol dispersion comprises dispersing megestrol particles in a liquid dispersion medium in which megestrol is poorly soluble, followed by applying mechanical means in the presence of grinding media to reduce the particle size of megestrol to the desired effective average particle size. The dispersion medium can be, for example, water, safflower oil, ethanol, t-butanol, glycerin, polyethylene glycol (PEG), hexane, or glycol.

The megestrol particles can be reduced in size in the presence of at least one surface stabilizer. Alternatively, the megestrol particles can be contacted with one or more surface stabilizers after attrition. Other compounds, such as a diluent, can be added to the megestrol/surface stabilizer composition either before, during, or after the size reduction process. Dispersions can be manufactured continuously or in a batch mode.

2. Precipitation to Obtain Nanoparticulate Megestrol Compositions

Another method of forming the desired nanoparticulate megestrol composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving megestrol in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Megestrol Compositions

Exemplary homogenization methods of preparing nanoparticulate active agent compositions are described in U.S. Pat. No. 5,510,118, for "Process of Preparing Therapeutic Compositions Containing Nanoparticles."

Such a method comprises dispersing megestrol particles in a liquid dispersion medium, followed by subjecting the dispersion to homogenization to reduce the particle size of the megestrol to the desired effective average particle size. The megestrol particles can be reduced in size in the presence of at least one surface stabilizer. Alternatively, the megestrol particles can be contacted with one or more surface stabilizers either before or after attrition. Other compounds, such as a diluent, can be added to the megestrol/surface stabilizer composition either before, during, or after the size reduction process. Dispersions can be manufactured continuously or in a batch mode.

D. Methods of Using Nanoparticulate Megestrol Formulations of the Invention

1. Applications of the Nanoparticulate Compositions of the Invention

The nanoparticulate megestrol compositions of the invention may be used as an appetite stimulant to treat wasting conditions or cachexia. As used herein, the term "wasting" is used to mean a condition where the patient is losing body mass as a side effect of a disease progression, a disease treatment, or other condition. Examples of conditions where wasting is prevalent include, but are not limited to, HIV or AIDS, cancer, cachexia and anorexia.

Additional conditions where the nanoparticulate megestrol compositions of the invention may be used include, but are not limited to, neoplastic diseases where the disease normally regresses or the patient's symptoms are normally reduced in response to megestrol, or any other progestin.

The nanoparticulate megestrol compositions of the invention may also be used to treat conditions such as breast cancer, endometrial cancer, uterine cancer, cervical cancer, prostate cancer, and renal cancer. As used herein, the term "cancer" is used as one of ordinary skill in the art would recognize the term. Examples of cancers include, but are not limited to, neoplasias (or neoplasms), hyperplasias, dysplasias, metaplasias, and hypertrophies. The neoplasms may be benign or malignant, and they may originate from any cell type, including but not limited to epithelial cells of various origin, muscle cells, and endothelial cells.

The present invention also provides methods of hormone replacement therapy in post-menopausal women, or in subjects after castration, comprising administering a nanoparticulate megestrol composition of the invention. Further, the compositions of the present invention may be used for ovarian suppression in several situations such as endometriosis, hirsutism, dysmenorrhea, and uterine bleeding.

The present invention also provides methods of oral contraception comprising administering a nanoparticulate megestrol composition of the invention. In one embodiment, the compositions of the invention are administered in combination with estrogen or a synthetic estrogen.

2. Dosage Forms of the Invention

The nanoparticulate megestrol compositions of the invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Moreover, the nanoparticulate megestrol compositions of the invention can be formulated into any suitable dosage form, including but not limited to liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

Nanoparticulate megestrol compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate megestrol compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid nanoparticulate megestrol dosage forms for oral administration include pharmaceutically acceptable emulsions, solutions, suspensions, syrups, and elixirs. In addition to megestrol, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

3. Dosage Quantities for the Nanoparticulate Megestrol Compositions of the Invention The present invention provides a method of achieving therapeutically effective plasma levels of megestrol in a subject at a lower dose than the standard commercial formulations. This can permit smaller dosing volumes depending on the megestrol concentration chosen. Such a method comprises orally administering to a subject an effective amount of a nanoparticulate megestrol composition.

The nanoparticulate megestrol composition, when tested in fasting subjects in accordance with standard pharmacokinetic practice, produces a maximum blood plasma concentration profile of megestrol of greater than about 30 ng/ml in less than about 5 hours after the initial dose of the composition.

As used herein, the phrase "maximum plasma concentration" is interpreted as the maximum plasma concentration that megestrol will reach in fasting subjects.

A suitable dose of megestrol, administered according to the method of the invention, is typically in the range of about 1 mg/day to about 1000 mg/day, or from about 40 mg/day to about 800 mg/day. Preferably, the therapeutically effective amount of the megestrol of this invention is about ⅙, about ⅕, about ¼, about ⅓$^{rd}$, or about ½ of the therapeutically effective amount of existing commercial megestrol formulations, e.g., Megace®.

"Therapeutically effective amount" as used herein with respect to a drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

One of ordinary skill will appreciate that effective amounts of megestrol can be determined empirically and can be employed in pure form or, where such forms exist, in pharmaceutically acceptable salt, ester, or prodrug form. Actual dosage levels of megestrol in the nanoparticulate compositions of the invention may be varied to obtain an amount of megestrol that is effective to obtain a desired therapeutic response for a particular composition and method of administration. The selected dosage level therefore depends upon the desired therapeutic effect, the route of administration, the potency of the administered megestrol, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

In the examples that follow, the value for D50 is the particle size below which 50% of the megestrol particles fall. Similarly, D90 is the particle size below which 90% of the megestrol particles fall.

The formulations in the examples that follow were also investigated using a light microscope. Here, "stable" nanoparticulate dispersions (uniform Brownian motion) were readily distinguishable from "aggregated" dispersions (relatively large, nonuniform particles without motion). Stable, as known in the art and used herein, means the particles don't substantially aggregate or ripen (increase in fundamental particle size).

Example 1

The purpose of this example was to describe preparation of nanoparticulate dispersions of megestrol acetate.

Formulations 1, 2, 3, 4 and 5, shown in Table 1, were milled under high energy milling conditions using a NanoMill® (Elan Drug Delivery, Inc.) (see e.g., WO 00/72973 for "Small-Scale Mill and Method Thereof") and a Dyno®-Mill (Willy Bachofen AG).

TABLE 1

| Formulation | Quantity of Megestrol | Identity and Quantity of Primary Surface Stabilizer | Identity and Quantity of Secondary Surface Stabilizer | Mean (nm) | D90 (nm) |
|---|---|---|---|---|---|
| 1 | 5% | 1% HPC-SL | 0.05% DOSS | 167 | 224 |
| 2 | 5% | 1% HPMC | 0.05% DOSS | 156 | 215 |
| 3 | 5% | 1% PVP | 0.05% DOSS | 167 | 226 |
| 4 | 5% | 1% Plasdone ® S630* | 0.05% DOSS | 164 | 222 |
| 5 | 5% | 1% HPMC | 0.05% SLS | 148 | 208 |

*Plasdone ® S630 (ISP) is a random copolymer of vinyl acetate and vinyl pyrrolidone.

Formulations 1-5 showed small, well-dispersed particles using the Horiba La-910 Laser Scattering Particle Size Distribution Analyzer (Horiba Instruments, Irvine, Calif.) and light microscopy. Formulations 1-5 were stable in electrolyte fluids and had acceptable physical stability at 5° C. for 4 weeks. Electrolyte fluids are representative of physiological conditions found in the human body. Formulations 1, 2, 3, and 4 also exhibited acceptable stability at 25° C. and 40° C. for 4 weeks. Formulation 5 exhibited acceptable stability at 40° C. for at least 3 weeks.

Example 2

This example compares the pharmacokinetic parameters of nanoparticulate megestrol acetate formulations of the present invention with conventional microparticulate formulations of megestrol acetate.

Twelve male beagles, at least twelve months of age, were divided into 2 groups based on whether they were fasting or being fed. The dogs were acclimated for thirteen days prior to dosing. The animals weighed approximately 11.4 to 14.3 kg at the time of dosing, and the dose was adjusted to 10 mg/kg. Water was available ad libitum. The animals were fasted (food only) for twelve to sixteen hours prior to dosing on day 1. On day 1, each dog was administered a formulation by gavage. Following dosing, the gavage tube was flushed with 18 ml of water. In the fed study, the animals were fed a high fat meal about 1 hour prior to dosing.

The dogs were subdivided into four groups, with each group receiving either Formulation A (nanoparticulate megestrol dispersion #1, comprising 4.0% megestrol acetate, 0.8% HPMC, and 0.4% DOSS), Formulation B (nanoparticulate megestrol dispersion #2, comprising 4.0% megestrol acetate, 0.8% HPMC, and 0.04% SLS), Formulation C (suspension of microparticulate megestrol acetate, Par Pharmaceutical, Inc., New York) or Formulation D (Megace® Oral Suspension, which is a suspension of microparticulate megestrol acetate).

Each formulation was adjusted to administer a dose of 10 mg/kg of megestrol acetate to the subject.

Prior to dosing, blood samples were taken from each subject. Blood samples were then collected from each subject at 15 and 30 minutes, as well as 1, 2, 3, 4, 6, 8, 24, 48, and 72 hours after dosing and centrifuged. Plasma was then separated and diluted when necessary, and subsequently analyzed for megestrol acetate by HPLC.

Tables 2 and 3 summarize the pharmacokinetic data of the four formulations administered to fasted dogs and fed dogs, respectively.

TABLE 2

Summary of Pharmacokinetic Data in Fasted Dogs

| Parameters | Formulation A<br>n = 3<br>(Mean ± SD) | Formulation B<br>n = 3<br>(Mean ± SD) | Formulation C<br>n = 3<br>(Mean ± SD) | Formulation D<br>n = 3<br>(Mean ± SD) |
|---|---|---|---|---|
| $AUC_{0-t}$ | 37774.23 ± 11648.60 | 21857.68 ± 10737.53 | 17395.95 ± 10428.73 | 10094.30 ± 1990.89 |
| $AUC_{0-inf}$ | 49408.88 ± 3392.80 | 27863.56 ± 15279.16 | 6948.48±* | 12007.13 ± 1923.80 |
| $C_{max}$ | 2209.74 ± 351.54 | 1563.02 ± 787.37 | 484.98 ± 321.70 | 339.92 ± 175.86 |
| $T_{max}$ | 0.83 ± 0.29 | 0.50 ± 0.00 | 18.67 ± 9.24 | 2.67 ± 0.58 |
| $t_{1/2}$ | 42.01 ± 33.81 | 30.09 ± 19.37 | 26.57±* | 25.59 ± 7.11 |
| $K_{el}$ | 0.025 ± 0.018 | 0.032 ± 0.024 | 0.026±* | 0.028 ± .0.007 |

$AUC_{0-t}$ (ng · hr/ml) = Area under the curve from time zero to the last measurable concentration;
$AUC_{0-inf}$ (ng · hr/ml) = Area under the curve from time zero to infinity;
$C_{max}$ (ng/ml) = Maximum plasma concentration;
$T_{max}$ (hr) = Time to occurrence of $C_{max}$;
$t_{1/2}$ (hr) = Apparent elimination half-life;
$K_{el}$ (1/hr) = elimination rate constant;
*n = 1.

TABLE 3

Summary of Pharmacokinetic Data in Fed Dogs

| Parameters | Formulation A<br>n = 3<br>(Mean ± SD) | Formulation B<br>n = 3<br>(Mean ± SD) | Formulation C<br>n = 3<br>(Mean ± SD) | Formulation D<br>n = 3<br>(Mean ± SD) |
|---|---|---|---|---|
| $AUC_{0-t}$ | 48543.56 ± 11608.55 | 36687.92 ± 12016.26 | 27332.11 ± 6488.79 | 31397.16 ± 5823.79 |
| $AUC_{0-inf}$ | 61734.90 ± 4918.52 | 42787.74 ± 14630.92 | 31720.98 ± 5580.32 | 40218.66 ± 8649.33* |
| $C_{max}$ | 3777.34 ± 2489.41 | 2875.82 ± 1334.32 | 2180.73 ± 406.28 | 2577.83 ± 665.31 |
| $T_{max}$ | 1.67 ± 2.02 | 3.00 ± 4.33 | 1.00 ± 0.00 | 0.83 ± 0.29 |
| $t_{1/2}$ | 34.35 ± 12.10 | 26.67 ± 7.80 | 26.16 ± 10.88 | 36.60 ± 9.62* |
| $K_{el}$ | 0.022 ± 0.009 | 0.028 ± 0.010 | 0.31 ± 0.16 | 0.20 ± 0.005 |

$AUC_{0-t}$ (ng · hr/ml) = Area under the curve from time zero to the last measurable concentration;
$AUC_{0-inf}$ (ng · hr/ml) = Area under the curve from time zero to infinity;
$C_{max}$ (ng/ml) = Maximum plasma concentration;
$T_{max}$ (hr) = Time to occurrence of $C_{max}$;
$t_{1/2}$ (hr) = Apparent elimination half-life;
$K_{el}$ (1/hr) = elimination rate constant;
*n = 2.

The results in the fasted dogs show that the nanoparticulate megestrol formulations (Formulations A and B) showed dramatically superior bioavailability, as evidenced by the superior AUC and $C_{max}$ results, as compared to the conventional microparticulate megestrol formulations (Formulations C and D). Formulation A, with a $C_{max}$ of 2210, had a maximum concentration more than 4½ times that of Formulation C (485), and a maximum concentration more than 6½ times that of Formulation D (340). Formulation B, with a $C_{max}$ of 1563, had a maximum concentration more than 3.2 times that of Formulation C (485), and a maximum concentration more than 4.6 times that of Formulation D (340). Also, Formulation A, with an AUC of 49,409 ng hr/mL, had an oral bioavailability more than 7 times that of Formulation C (6948 ng hr/mL) and an oral bioavailability of more than 4 times that of Formulation D (12007 ng hr/mL). Formulation B, with an AUC of 27,864 ng hr/mL, had an oral bioavailability more than 4 times that of Formulation C (6949 ng hr/mL) and an oral bioavailability more than 2 times that of Formulation D (12,007 ng hr/mL).

In addition, in the fasted dogs the nanoparticulate megestrol formulations (Formulations A and B) showed dramatically superior faster onset of action, as evidenced by the superior $T_{max}$ results, as compared to the conventional microparticulate megestrol formulations (Formulations C and D). Formulation A, with a $T_{max}$ of 0.83 hr, reached a maximum concentration of megestrol in less than $\frac{1}{20}^{th}$ the time of Formulation C (18.67 hr), and in less than $\frac{1}{3}^{rd}$ the time of Formulation D (2.67 hr). Formulation B, with a $T_{max}$ of 0.50 hr, reached a maximum concentration in less than $\frac{1}{37}^{th}$ the time of Formulation C (18.67 hr), and in less than $\frac{1}{5}^{th}$ the time of Formulation D (2.67 hr).

Similarly, the results in the fed dogs show that the nanoparticulate megestrol formulations (Formulations A and B) showed dramatically superior bioavailability, as evidenced by the superior AUC and $C_{max}$ results, as compared to the conventional microparticulate megestrol formulations (Formulations C and D). Formulation A, with a $C_{max}$ of 3777, had a maximum concentration of about more than 1.7 times that of Formulation C (2181), and a maximum concentration of about more than 1.5 times that of Formulation D (2578). Formulation B, with a $C_{max}$ of 2876, had a maximum concentration of about more than 1.3 times that of Formulation C (2181), and a maximum concentration of about more than 1.1 times that of Formulation D (2578). Formulation A, with an AUC of 61,735 ng hr/mL, had an oral bioavailability of more than 1.9 times that of Formulation C (31721 ng hr/mL) and more than 1.5 times that of Formulation D (40219 ng hr/mL). Formulation B, with an AUC of 42788 ng hr/mL, had an oral bioavailability of more than 1.3 times that of Formulation C (31721 ng hr/mL) and an oral bioavailability of more than 1.1 times that of Formulation D (40218 ng hr/mL).

Example 3

This example demonstrates the physical stability of megestrol acetate dispersions at various concentrations and with the addition of sucrose, flavoring, and preservatives.

Megestrol acetate was milled under high energy milling conditions using a NanoMill™2 System (Elan Drug Delivery, Inc.) in the presence of a preservative/buffer system consisting of sodium benzoate, citric acid monohydrate, and sodium citrate dihydrate. After milling, the resulting dispersion was diluted with water, sucrose, flavoring, and additional preservative/buffer to prepare dispersions containing 3% (w/w), 5% (w/w), or 9% (w/w) megestrol acetate. The resulting formulations are shown in Table 4. The physical stability of the formulations was then monitored at 25° C., 40° C., and 50° C.

Example 4

The purpose of this Example was to demonstrate the improved viscosity characteristics of the dispersions of this invention.

The viscosities of three formulations of this invention (E, F, and G as described in Example 3) and two conventional commercial formulations (Formulations C and D as described in Example 2) were determined using a rheometer (model CVO-50, Bohlin Instruments). The measurements were performed at a temperature of 20° C. using a double gap (40/50) geometry.

The viscosities of the Formulations of this invention were found to be nearly Newtonian (i.e., the viscosity being independent of shear rate), and were 1.5, 2.0, and 3.5 mPa s for the 30, 50, and 90 mg/mL concentrations, respectively.

The viscosity dependence on concentration is illustrated in FIG. 1.

The commercial formulations C and D were shear thinning in nature. Such samples cannot be characterized by a single viscosity but rather a series of viscosities measured at differ-

TABLE 4

Formulation Summary

| | Concentrated | Diluted, Flavored Dispersions | | |
|---|---|---|---|---|
| API and Excipients | Nanoparticle Dispersion g/kg | Formulation E 3% Dispersion g/kg | Formulation F 5% Dispersion g/kg | Formulation G 9% Dispersion g/kg |
| Megestrol Acetate, USP | 325.000 | 30.000 | 50.000 | 90.000 |
| Hydroxypropyl Methylcellulose, USP | 65.000 | 6.000 | 10.000 | 18.000 |
| Docusate Sodium, USP | 3.250 | 0.300 | 0.500 | 0.900 |
| Sodium Benzoate, USP | 1.214 | 1.826 | 1.777 | 1.681 |
| Sodium Citrate Dihydrate, USP | 0.910 | 0.091 | 0.089 | 0.084 |
| Citric Acid Monohydrate, USP | 0.061 | 1.369 | 1.333 | 1.260 |
| Sucrose, USP | | 50.000 | 50.000 | 50.000 |
| Natural and Artificial Lemon Flavor | | 0.400 | 0.400 | 0.400 |
| Artificial Lime Flavor | | 0.400 | 0.400 | 0.400 |
| Purified Water, USP | 604.600 | 909.614 | 885.500 | 837.280 |

API = active pharmaceutical ingredient

Figure 2:
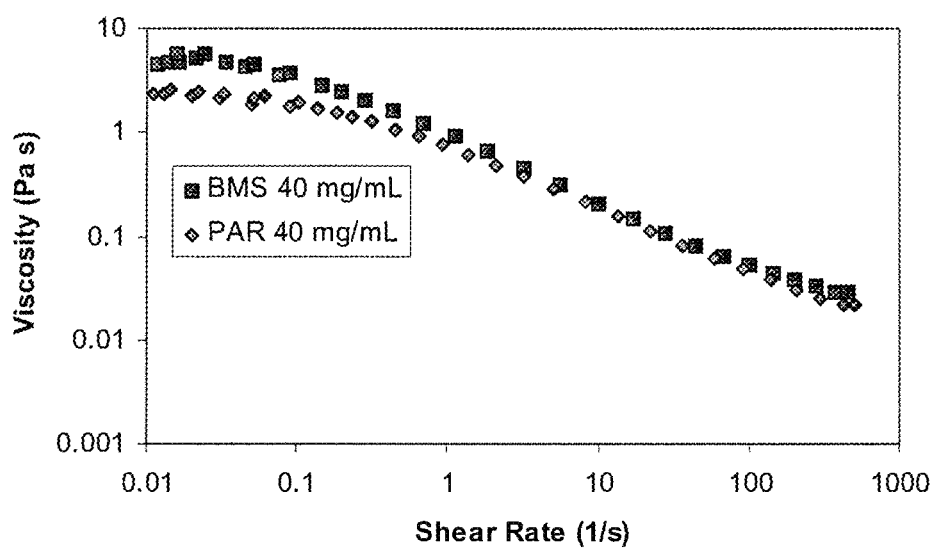
FIG. 2: Illustrates viscosity in units of Pa s as a function of shear rate for two commercial samples, Bristol Myers Squibb and Par Pharmaceuticals, both at an active concentration of 40 mg/mL.

Particle size measurements (Table 5) were used to assess the physical stability. The results show almost no increase in the mean particle size at either 25° C. or 40° C., and only a slight increase in the mean particle size at 50° C. 126 days of stability measurements were obtained for the 5% and 9% dispersions and 33 days of stability were obtained for the 3% dispersion, which was prepared at a later date.

ent shear rates. This is most conveniently illustrated as viscosity-shear rate curves as shown in FIG. 2.

The commercial samples and the three formulations of this invention are compared in Table 6 below. Viscosities are in units of mPa s.

TABLE 5

Mean particle size (nm)

| | 3% Dispersion | | | 5% Dispersion | | | 9% Dispersion | | |
|---|---|---|---|---|---|---|---|---|---|
| | 25° C. | 40° C. | 50° C. | 25° C. | 40° C. | 50° C. | 25° C. | 40° C. | 50° C. |
| 0 days | 148 | 148 | 148 | 169 | 169 | 169 | 169 | 169 | 169 |
| 30 days | | | | 172 | 171 | 187 | 172 | 170 | 179 |
| 33 days | 141 | 144 | 173 | | | | | | |
| 126 days | | | | 171 | 174 | 188 | 168 | 175 | 182 |

TABLE 6

Shear Rates of Commercial Megestrol Formulations (D and C) and the
Nanoparticulate Megestrol Formulations of the Invention (E, F, & G)

| Shear Rate $s^{-1}$ | Commercial Samples | | Formulations E, F, & G | | |
|---|---|---|---|---|---|
| | Formulation D (mPa s) | Formulation C (mPa s) | (E) 30 mg/mL (mPa s) | (F) 50 mg/mL (mPa s) | (G) 90 mg/mL (mPa s) |
| 0.1 | 4010 | 2860 | 1.5 | 2.0 | 3.5 |
| 1 | 929 | 723 | " | " | " |
| 10 | 215 | 183 | " | " | " |
| 100 | 49.9 | 46.3 | " | " | " |

* These samples were not measured at the 0.1 and 1 $s^{-1}$ shear rates (the shear range was ca 2 to 100 $s^{-1}$) but the assessment that these exhibit Newtonian flow properties justifies the entries.

Example 5

The purpose of this Example was to visually demonstrate the difference between the viscosity characteristics of liquid megestrol formulations of the invention as compared to conventional liquid megestrol formulations.

Figure 3:
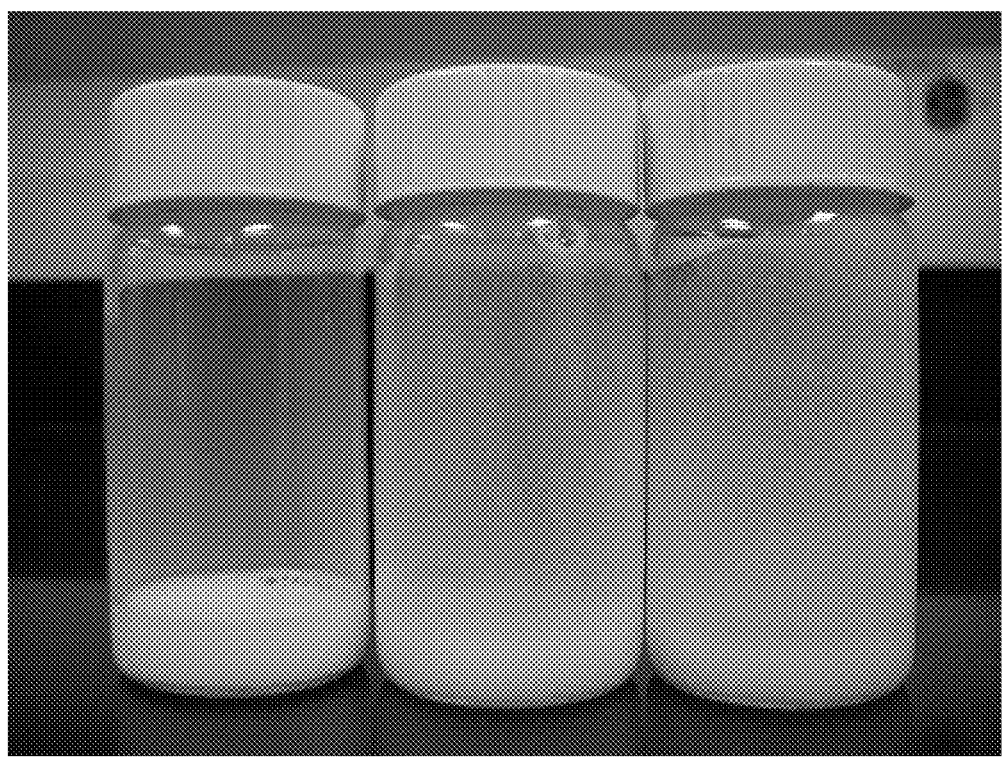
FIG. 3: Shows a photograph of, from left to right, a nanoparticulate dispersion of megestrol acetate, a commercial sample of megestrol acetate marketed by Par Pharmaceuticals, and a commercial sample of megestrol acetate marketed by Bristol Myers Squibb.

A sample of a 50 mg/mL nanoparticulate dispersion of megestrol acetate and two conventional commercial formulations at 40 mg/mL (Formulations C and D as described in Example 2) were each placed in a vial, which was then shaken. Attached as FIG. 3 is a photograph of the three vials, which from left to right are the nanoparticulate megestrol acetate dispersion, Formulation C, and Formulation D.

The vial with the nanoparticulate dispersion shows a thin, silky, almost shear film coating the vial. In contrast, the vials containing the two commercial formulations show a gritty residue coating. Such a gritty residue is the same residue which coats a patient's mouth and throat upon administration. Such a coating is highly unpleasant, particularly for patients suffering from wasting (i.e., unable to eat). Thus, FIG. 3 visually demonstrates the appeal of a liquid oral nanoparticulate megestrol formulation of the invention as compared to conventional commercial liquid oral megestrol formulations.

Example 6

The purpose of this example was to prepare nanoparticulate compositions of megestrol acetate using various surface stabilizers.

5% megestrol acetate (Par Pharmaceuticals, Inc.) was combined with 1.25% of various surface stabilizers: tyloxapol (Sterling Organics), Tween 80 (Spectrum Quality Products), Pluronic F-108 (BASF), Plasdone S-630 (ISP), hydroxypropylmethylcellulose (HPMC) (Shin Etsu), hydroxypropylcellulose (HPC-SL) (Nippon Soda Co., Ltd.), Kollidon K29/32 (polyvinylpyrrolidone) (ISP), or lysozyme (Fordras).

For each combination of megestrol acetate and surface stabilizer, the surface stabilizer was first dissolved in 7.875 g water for injection (WFI) (Abbott Laboratories, Inc.), followed by the addition of the milling media, PolyMill™-500 (Dow Chemical, Co.), and 0.42 g megestrol.

The slurries were charged into each of eight 18 cc NanoMill® (Elan Drug Delivery) chambers and milled for 30 min. Upon completion of milling the dispersions were harvested with a 26 gauge needle yielding the following particle sizes shown in Table 7.

All particle size distribution analyses were conducted on a Horiba LA-910 Laser Light Scattering Particle Size Distribution Analyzer (Horiba Instruments, Irvine, Calif.). RO-water was utilized as the liquid dispersing medium and a flow-through sample cell was used for all measurements. All samples were assayed in 150 cc liquid medium.

TABLE 7

| Megestrol Conc. | Surface Stabilizer/Conc. | Mean Particle Size |
|---|---|---|
| 5% | tyloxapol; 1.25% | 214 nm |
| 5% | Tween 80; 1.25% | 210 nm |
| 5% | Pluronic F-108; 1.25% | 459 nm |
| 5% | Plasdone S-630; 1.25% | 292 nm |
| 5% | HPMC; 1.25% | 314 nm |
| 5% | HPC-SL; 1.25% | 623 nm |
| 5% | PVP K29/32; 1.25% | 24816 nm |
| 5% | lysozyme; 1.25% | 179 nm |

The results show that tyloxapol, Tween 80, and lysozyme produced small particles without substantial aggregation. Pluronic F-108, Plasdone S-630, HPMC, HPC-SL, and K29/32 had larger particle sizes, indicating that aggregation was occurring. Thus, at the particular concentration of drug and surface stabilizer, using the described milling method, Pluronic F-108, Plasdone S-630, HPMC, HPC-SL, and K29/32 were not preferable surface stabilizers. These surface stabilizers may be useful in nanoparticulate compositions of megestrol at different drug or surface stabilizer concentrations, or when used in conjunction with another surface stabilizer.

Example 7

The purpose of this example was to prepare nanoparticulate compositions of megestrol acetate using various surface stabilizers.

Megestrol acetate (Par Pharmaceuticals, Inc.) and various surface stabilizers, as shown in Table 8, were combined and milled, followed by determination of the particle size and stability of the resulting composition. Materials were obtained as in Example 6.

All of the samples were milled using a Dyno®-Mill (Model KDL-Series, Willy Bachofen AG, Basel, Switzerland) equipped with a 150 cc stainless steel batch chamber. Cooling water (approximate temperature 5° C.) was circulated through the mill and chamber during operation.

All particle size distribution analyses were conducted on a Horiba LA-910 Laser Light Scattering Particle Size Distribution Analyzer (Horiba Instruments, Irvine, Calif.), as described above in Example 6.

Qualitative microscopic assessments of the formulations were performed using a Leica light microscope (Type 301-371.010). Sample preparation involved diluting the product dispersions in RO-water and dispensing about 10 μL onto a glass slide. Oil immersion was utilized in conjunction with 1000× magnification.

The physical stability was assessed by storing the dispersion is 20 ml glass scintillation vials in a temperature/humidity controlled chamber at either 5° C., (25° C./60% RH), (40° C./75% RH), (50° C./75% RH), or 55° C. Samples were taken at varying time intervals and the particle size was analyzed.

For all formulations, the surface stabilizer(s) was first dissolved in WFI (Abbott Laboratories, Inc.) (75.0 g for Exp. Nos. 1, 2, 3, 7, and 8; 75.2 g for Exp. Nos. 4 and 9; 74.9 g for Exp. Nos. 5 and 6; 70.3 g for Exp. Nos. 10 and 11), followed by combining the surface stabilizer solution megestrol acetate and PolyMill™-500 polymeric grinding media. This mixture was then added to the appropriate milling chamber, milled for the time period shown in Table 8, followed by harvesting and vacuum filtering of the megestrol acetate dispersion.

observed, Tween 80, tyloxapol, and Pluronic F127 were deemed not suitable surface stabilizers at the described drug/surface stabilizer concentrations prepared under the conditions described above.

The HPC-SL formulation (Exp. No. 8) showed substantial aggregation indicating that a secondary charged stabilizer would be needed. SLS was added (Exp. No. 6) and the new formulation grew from 167 to 194 nm after storage at 40° C. for 15 days and did not show any substantial aggregation upon incubation in either 0.01N HCl or normal saline. The SLS appeared effective at preventing the aggregation but the sample showed some particle size growth.

TABLE 8

| Exp. No. | Megestrol Conc. | Surface Stabilizer(s) and Conc. | Milling Time | Mean Particle Size | Stability |
|---|---|---|---|---|---|
| 1 | 5% | 1.25% lysozyme | 20 min. | 209 nm | The sample showed substantial aggregation after incubation in normal saline for 30 minutes as determined by optical microscopy. |
| 2 | 5% | 1.25% Tween 80 | 75 min. | 157 nm | Upon storage at 5° C. for 15 days the sample grew to a mean diameter of 577 nm. |
| 3 | 5% | 1.25% tyloxapol | 2 hrs. | 208 nm | Optical microscopoy revealed the presence of elongated "needle-like" crystals. |
| 4 | 5% | 1% Pluronic F127 | 2 hrs. | 228 nm | Upon storage at 25° C. for 5 days the sample grew to a mean diameter of 308 nm. |
| 5 | 5% | 1.25% HPMC 0.0625% SLS[1] | 75 min. | 161 nm | Upon storage at 40° C. for 19 days, the sample grew to a mean diameter of 171 nm. Incubation for 30 minutes at 40° C. in 0.01N HCl or normal saline resulted in particle sizes of 164 nm and 209 nm, respectively. |
| 6 | 5% | 1.25% HPC-SL, 0.05% SLS | 60 min. | 167 nm | Upon storage at 40° C. for 15 days, the sample grew to a mean diameter of 194 nm. Incubation for 30 minutes at 40° C. in 0.01N HCl or normal saline resulted in particle sizes of 183 nm and 179 nm, respectively. |
| 7 | 5% | 1.25% HPMC | 45 min. | 185 nm | Upon storage at 40° C. for 6 days, the sample grew to a mean diameter of 313 nm. Incubation for 30 minutes at 40° C. in 0.01N HCl or normal saline resulted in particle sizes of 2041 nm and 1826 nm, respectively. Optical microscopy revealed aggregation in both the saline and HCl samples. |
| 8 | 5% | 1.25% HPC-SL | 45 min. | 176 nm | Upon storage at 40° C. for 6 days, the sample grew to a mean diameter of 244 nm. Incubation for 30 minutes at 40° C. in 0.01N HCl or normal saline resulted in particle sizes of 873 nm and 524 nm, respectively. Optical microscopy revealed aggregation in both the saline and HCl samples. |
| 9 | 5% | 1% HPMC 0.05% SLS | 70 min. | 152 nm | Incubation for 30 minutes at 40° C. in 0.01N HCl or normal saline resulted in particle sizes of 155 nm and 539 nm, respectively. Optical microscopy confirmed that aggregation was present in the sample incubated in saline. |
| 10 | 10% | 2% HPMC 0.1% DOSS[2] | 70 min. | 150 nm | Following harvesting the sample was diluted to 4% API by adding WFI. Upon storage at 40° C. for 40 days, the sample had a mean diameter of 146 nm. Optical microscopy revealed small, well dispersed particles. |
| 11 | 10% | 2% HPMC 0.1% SLS | 70 min. | 146 nm | Upon storage at 40° C. for 19 days, the sample had a mean diameter of 149 nm. Optical microscopy revealed small, well dispersed particles. |
| 12 | 10% | 4% lysozyme | 60 min. | 108 nm | Upon storage at 40° C. for 9 days the sample had a mean diameter of 124 nm. Optical microscopy revealed small, well dispersed particles. |

[1]Sodium lauryl sulfate (Spectrum Quality Products)
[2]Dioctyl Sodium Sulfosuccinate (Cytec)

The results shown in Table 8 indicate that the use of lysozyme (Exp. No. 1) as a surface stabilizer resulted in small well dispersed particles with a mean particle size of 209 nm, but the formulation showed aggregation when diluted into a normal saline solution. A megestrol acetate/tyloxapol sample was also stable at higher drug and stabilizer concentrations (Exp. No. 12).

Tween 80, tyloxapol, and Pluronic F127 (Exp. Nos. 2, 3, and 4) were effective primary surface stabilizers and produced well-dispersed particles without significant aggregation. Stability measurements, however, revealed rapid crystal growth for all three stabilizers. 5% megestrol acetate/1.25% Tween 80 grew from 157 nm to 577 nm after 15 days at 5° C. 5% megestrol acetate/1.25% tyloxapol showed needle-like crystals when observed under optical microscopy. 5% megestrol acetate/1.25% Pluronic F127 grew from 228 nm to 308 nm after 5 days at 25° C. Because of the rapid crystal growth The HPMC formulation (Exp. No. 7) showed substantial aggregation indicating that a secondary charged stabilizer would be needed. SLS was added (Exp. Nos. 5 and 11), and the new formulations showed only minimal growth from 161 nm to 171 nm (Exp. No. 5), and from 146 to 149 nm (Exp. No. 11), after storage at 40° C. for 19 days. In addition, the composition of Exp. No. 5 did not show any substantial aggregation upon incubation in either 0.01N HCl or normal saline. The SLS was effective at preventing the aggregation without causing significant crystal growth.

An attempt was made to reduce the concentration of the primary and secondary stabilizers (Exp. No. 9) and resulted in a post-milling mean diameter of 152 nm. Incubation for 30 minutes at 40° C. in normal saline resulted in particle sizes of 539 nm. Optical microscopy confirmed that aggregation was present in the sample incubated in saline.

Docusate sodium (DOSS) was tried as a secondary stabilizer (Exp. No. 10) and resulted in well-dispersed particles with a mean diameter of 150 nm. Upon storage at 40° C. for 40 days, the sample had a mean diameter of 146 nm. Optical microscopy revealed small, well-dispersed particles. DOSS seemed to result in even less particle size growth than SLS.

Example 8

The purpose of this example was to prepare nanoparticulate compositions of megestrol acetate using various surface stabilizers and further including preservatives or excipients.

The materials and methods were the same as in Example 7, except that for several of the examples different sources of megestrol acetate were used (See Table 9). In addition, for Exp. Nos. 5, a NanoMill® milling system (Elan Drug Delivery) was used. Several different combinations of megestrol acetate, surface stabilizer(s), and one or more preservatives or excipients were prepared, following by testing the compositions for particle size and stability.

The surface stabilizer(s) and one or more preservatives were first dissolved in WFI, followed by combining the solution with megestrol acetate and the grinding media. This mixture was then added to the milling chamber and milled for the time period set forth in Table 9, below.

For several of the experiments, following milling the megestrol acetate dispersion was combined with a flavored suspension. The stability of the resultant composition was then evaluated.

The formulation details and results are shown in Table 9, below.

In Exp. No. 1 of Table 9, a sweetened, flavored dispersion was prepared by mimicking the current commercial formulation of megestrol acetate that contains sucrose, xanthan gum, glycerol, lemon and lime flavors, and is preserved and buffered with sodium benzoate and citric acid. Upon storage at 40° C. for 24 days the sample showed aggregation with a mean diameter of 837 nm. Incubation for 30 minutes at 40° C. in 0.01N HCl or normal saline resulted in particle sizes of 206 nm and 3425 nm, respectively. Optical microscopy confirmed that the sample incubated in saline had aggregated. The aggregation upon storage indicated that this particular combination of drug and surface stabilizer, at the concentrations used and methodology employed to make the compositions, would not be an effective formulation.

For Exp. Nos. 4 and 5, the formulation was scaled-up in a NanoMill™-2 system to determine if the scale-up would effect the physical stability. Two different sources of megestrol acetate were tested: Pharmacia and Pharmabios. The product of Exp. No. 4 had a mean diameter of 160 nm without ultrasound. Upon storage at 50° C. for 44 days the mean diameter was 190 nm. The composition of Exp. No. 5 had a post-milling mean diameter of 147 nm without ultrasound. Upon storage at 50° C. for 44 days the mean diameter was 178 nm. Both sources of active agent milled effectively and showed little particle size growth even at 50° C.

The results of Examples 6 and 7 showed that high energy milling with polymeric attrition media could be used to pro-

TABLE 9

| Exp. | Megestrol Conc. | Surface Stabilizer(s) and Conc. | Preservatives/Excipients | Milling Time | Mean Particle Size | Stability |
|---|---|---|---|---|---|---|
| 1 | 10% | 2% HPMC 0.1% DOSS | Sodium Benzoate (0.4 g), Sodium Citrate Dihydrate (20 mg) Citric Acid Monohydrate (0.3 g) | 75 min | 146 nm | After milling a flavored suspension was prepared by adding sucrose (2.5 g), xanthan gum (0.113 g), glycerol (13.75 g), lemon flavor (0.1 g), WFI (18.6 g), and 20.0 g of the milled dispersion. Upon storage at 40° C. for 24 days, the sample showed aggregation with a mean diameter of 837 nm. Incubation for 30 minutes at 40° C. in 0.01 N HCl or normal saline resulted in particle sizes of 206 nm and 3425 nm, respectively. Optical microscopy confirmed that the sample incubated in saline had aggregated. |
| 2 | 25% | 5% HPMC 0.05% DOSS | Sodium Benzoate (0.11 g) Citric Acid Monohydrate (0.08 g) | 95 min. | See right column. | 16 g of the milled drug dispersion was combined with sucrose (5 g), lime flavor (80 mg), and WFI (78.9 g). The diluted drug dispersion had a mean diameter of 192. After 6 days at 55° C. the particles had a mean diameter of 10 microns, indicating substantial aggregation |
| 3 | 25% | 5% HPMC, 0.15% DOSS | Sodium Benzoate (0.11 g) Citric Acid Monohydrate (0.08 g) | 95 min. | See right column. | 16 g of the milled drug dispersion was combined with sucrose (5 g), lime flavor (80 mg), and WFI (78.9 g). The diluted drug dispersion had a mean diameter of 173 nm. After 12 days at 55° C. the particles had a mean diameter of 295 nm. |
| 4 | 32.5%[1] | 6.5% HPMC 0.33% DOSS | Sodium Benzoate (13.07 g) Sodium Citrate Dihydrate (0.65 g) Citric Acid Monohydrate (9.8 g) | 15.5 hrs | 160 nm | Upon storage at 50° C. for 44 days, the mean diameter was 190 nm. |
| 5 | 32.5% | 6.5% HPMC 0.33% DOSS | Sodium Benzoate (9.71 g) Sodium Citrate Dihydrate (0.49 g) Citric Acid Monohydrate (7.28 g) | 12 hrs | 147 nm | Upon storage at 50° C. for 44 days the mean diameter was 178 nm. |

[1]Pharmacia
[2]Pharmabios duce stable nanoparticulate colloidal dispersions of megestrol acetate suitable for oral administration to animals or humans. The primary stabilizer HPMC required the presence of DOSS or SLS to prevent aggregation at the concentrations of drug and stabilizer tested (other combinations of drug and HPMC concentrations may result in a stable composition without the addition of a second surface stabilizer). In general, average particle sizes of less than about 160 nm could be obtained. Tests conducted with two sources of megestrol acetate revealed that both sources milled effectively and exhibited excellent physical stability.

Based on mean particle size, physical stability, and the pre-clinical dog study, the best nanoparticulate megestrol acetate formulation for commercial development, based on the results of the data given in the examples, consisted of 32.5% megestrol acetate, 6.5% HPMC, and 0.325% DOSS (i.e., a drug:HPMC ratio of 1:5 and a drug:DOSS ratio of 1:100. The formulation milled effectively in the presence of preserved water (0.2% sodium benzoate, 0.01% sodium citrate dihydrate, and 0.15% citric acid monohydrate). Upon dilution with preserved water, flavors, and sucrose none of the dispersions showed severe aggregation, except for the dispersions containing xanthan gum (data not shown) or low levels of DOSS. The alcohol-based flavors did not effect the physical stability nor did several freeze-thaw cycles (data not shown).

Example 9

This example compares the pharmacokinetic parameters of nanoparticulate megestrol acetate formulations of the invention with a conventional microparticulate formulation of megestrol acetate. Results were obtained from a fasted study group consisting of 36 male subjects, 18 years of age or older. For a fed study group, results from 32 subjects were analyzed.

Subjects in the fasted study group and the fed study group were administered study drugs in four successive periods. Treatment A (1×150 mg drug as 5 ml of a 3% megestrol acetate nanoparticulate formulation) was administered in the first period. Reference Treatment B (1×800 mg drug as 20 ml of a 4% megestrol acetate Megace® Oral Suspension) was administered in the second period. Treatment C (1×250 mg drug as 5 ml of a 5% megestrol acetate nanoparticulate formulation) was administered in the third period. Treatment D (1×450 mg drug as 5 ml of a 9% megestrol acetate nanoparticulate formulation) was administered in the fourth period. The formulations of Treatments A, C, and D are listed in Table 10 below, with particle size information (microns) provided in Table 11.

In each period, subjects were confined from at least 10 hours prior to drug administration to after the last sample collection. In the fasted study group, no food was consumed from at least 10 hours before dosing to at least 4 hours after dosing. In the fed study group, a high-calorie breakfast (containing about 800 to 1000 calories, approximately 50% of which were from fat) was served within 30 minutes prior to dosing; dosing occurred within 5 minutes after the breakfast was completed. A controlled meal was served to both groups after 4 hours after dosing, and standard meals were served at appropriate times thereafter. The meals in all four periods were identical. Subjects in the fasted study group were not allowed fluid intake from 1 hour before dosing to 1 hour after. Subjects in the fed study group were also not allowed fluid intake during this period except for fluids provided with the high-calorie breakfast. Water was provided ad libitum to both study groups at all other times.

Blood samples were obtained before dosing, at half-hourly intervals in the 6 hours following dosing, and at 7, 8, 12, 16, 20, 24, 36, 48, 72, and 96 hours after dosing. Megestrol acetate in plasma samples was then determined.

Table 12 below summarizes pharmacokinetic data for the fasted study group, and Table 13 below summarizes pharmacokinetic data for the fed study group.

Treatments A, C, and D in fasting subjects produced dose-normalized values for $AUC_{0-t}$ and $AUC_{0-inf}$ that were approximately twice those of Reference Treatment B. Maximum dose-normalized megestrol acetate concentrations in Treatments A, C, and D were approximately 9 to 12 times that of Reference Treatment B. The maximum megestrol acetate concentration for the 150 mg-dose of Treatment A was approximately twice that of the 800 mg-dose of reference Treatment B. Moreover, comparable values of $AUC_{0-t}$ and $AUC_{0-inf}$ were observed for the 450 mg-dose of Treatment D and the 800 mg-dose of Reference Treatment B.

Treatments A, C, and D in fed subjects produced dose-normalized values for $AUC_{0-t}$ and $AUC_{0-inf}$ that were approximately 8 to 10% greater than those of Reference Treatment B. Maximum dose-normalized megestrol acetate concentrations in Treatments A, C, and D were approximately 38 to 46% greater than that of Reference Treatment B. Megestrol acetate onset for Treatments A, C, and D was comparable to Reference Treatment B.

Nanoparticulate megestrol acetate formulations, therefore, exhibited superior oral bioavailability, relative to the Megace® Oral Suspension, in fasting and fed human subjects.

TABLE 10

Formulations for Megestrol Acetate Oral Suspension 3, 5% and 9%

| | Strengths | | |
|---|---|---|---|
| Ingredients | 3% w/w (30 mg/mL) | 5% w/w (50 mg/mL) | 9% w/w (90 mg/mL) |
| Megestrol Acetate | 3.000 | 5.000 | 9.000 |
| Hydroxypropyl Methylcellulose | 0.600 | 1.000 | 1.800 |
| Docusate Sodium | 0.030 | 0.050 | 0.090 |
| Sodium Benzoate | 0.183 | 0.178 | 0.168 |
| Sodium Citrate Dihydrate | 0.009 | 0.009 | 0.008 |
| Citric Acid Monohydrate | 0.137 | 0.133 | 0.126 |
| Sucrose | 5.000 | 5.000 | 5.000 |
| Natural and Artificial Lemon Flavor | 0.040 | 0.040 | 0.040 |
| Artificial Lime Flavor | 0.040 | 0.040 | 0.040 |
| Purified Water | 90.961 | 88.550 | 83.727 |
| TOTAL | 100.000 | 100.000 | 100.000 |

TABLE 11

Particle Size Data for the Megestrol Acetate Oral Suspensions*

| | Strength 30 mg/g | | | Strength 50 mg/g | | | Strength 90 mg/g | | |
|---|---|---|---|---|---|---|---|---|---|
| | d (0.1) | d (0.5) | d (0.9) | d (0.1) | d (0.5) | d (0.9) | d (0.1) | d (0.5) | d (0.9) |
| Initial | 0.068 | 0.123 | 0.223 | 0.069 | 0.125 | 0.229 | 0.068 | 0.124 | 0.227 |
| ACC/1 month | 0.070 | 0.129 | 0.237 | 0.070 | 0.127 | 0.231 | 0.070 | 0.127 | 0.230 |
| ACC/2 months | 0.070 | 0.127 | 0.231 | 0.070 | 0.127 | 0.233 | 0.073 | 0.126 | 0.221 |
| ACC/3 months | 0.070 | 0.129 | 0.237 | 0.070 | 0.128 | 0.235 | 0.070 | 0.128 | 0.234 |
| RT 3 months | 0.070 | 0.128 | 0.237 | 0.073 | 0.128 | 0.224 | 0.067 | 0.121 | 0.223 |

*All particle sizes are given in microns. "d (0.1)" means distribution of smallest 10% of the particles, i.e., "d (0.1)" 10 μm means 10% of the particles are less than 10%. Similarly, "d (0.5)" means distribution of the smallest 50% of the particles, and "d (0.9)" means distribution of the smallest 90% of the particles. Thus, "d (0.9)" means that 90% of the particles are less than XX μm.

TABLE 12

Summary of Pharmacokinetic Data in Fasted Human Subjects*

| Parameters | Treatment A (Mean ± SD) | Ref. Treatment B (Mean ± SD) | Treatment C (Mean ± SD) | Treatment D (Mean ± SD) |
|---|---|---|---|---|
| $AUC_{0-t}$ | 2800 ± 900 | 7000 ± 5000 | 4700 ± 1800 | 8500 ± 3200 |
| $AUC_{0-inf}$ | 3100 ± 1000 | 9000 ± 9000 | 5200 ± 2100 | 9000 ± 4000 |
| $C_{max}$ | 410 ± 120 | 190 ± 110 | 650 ± 200 | 950 ± 270 |
| $T_{max}$ | 1.7 ± 0.9 | 6 ± 6 | 1.6 ± 1.0 | 1.7 ± 1.1 |
| $t_{1/2}$ | 35 ± 13 | 31 ± 19 | 34 ± 10 | 34 ± 12 |
| $K_{el}$ | 0.023 ± 0.011 | 0.026 ± 0.009 | 0.022 ± 0.008 | 0.023 ± 0.008 |

$AUC_{0-t}$ (ng · hr/ml) = Area under the curve from time zero to the last measurable concentration;
$AUC_{0-inf}$ (ng · hr/ml) = Area under the curve from time zero to infinity;
$C_{max}$ (ng/ml) = Maximum plasma concentration;
$T_{max}$ (hr) = Time to occurrence of $C_{max}$;
$t_{1/2}$ (hr) = Apparent elimination half-life;
$K_{el}$ (1/hr) = Elimination rate constant;
*n = 36.

TABLE 13

Summary of Pharmacokinetic Data in Fed Human Subjects*

| Parameters | Treatment A (Mean ± SD) | Ref. Treatment B (Mean ± SD) | Treatment C (Mean ± SD) | Treatment D (Mean ± SD) |
|---|---|---|---|---|
| $AUC_{0-t}$ | 3500 ± 1100 | 17000 ± 5000 | 5700 ± 1600 | 10500 ± 3000 |
| $AUC_{0-inf}$ | 3900 ± 1300 | 19000 ± 6000 | 6300 ± 2000 | 12000 ± 4000 |
| $C_{max}$ | 380 ± 140 | 1400 ± 400 | 590 ± 170 | 1080 ± 290 |
| $T_{max}$ | 3.8 ± 3.5 | 3.9 ± 0.9 | 3.4 ± 1.7 | 3.2 ± 1.7 |
| $t_{1/2}$ | 35 ± 12 | 33 ± 9 | 35 ± 10 | 38 ± 12 |
| $K_{el}$ | 0.023 ± 0.013 | 0.023 ± 0.007 | 0.023 ± 0.009 | 0.021 ± 0.008 |

$AUC_{0-t}$ (ng · hr/ml) = Area under the curve from time zero to the last measurable concentration;
$AUC_{0-inf}$ (ng · hr/ml) = Area under the curve from time zero to infinity;
$C_{max}$ (ng/ml) = Maximum plasma concentration;
$T_{max}$ (hr) = Time to occurrence of $C_{max}$;
$t_{1/2}$ (hr) = Apparent elimination half-life;
$K_{el}$ (1/hr) = Elimination rate constant;
*n = 32.

Example 10

This example compares the pharmacokinetic parameters of a nanoparticulate megestrol acetate formulations to a conventional microparticulate formulation of megestrol acetate (Megace® by Bristol Myers Squibb Co.). Results were obtained from a fasted study group consisting of 33 male subjects, 18 years of age or older.

The nanoparticulate megestrol acetate compositions were prepared as described in Example 10.

Subjects were administered study drugs in four successive periods. Treatment A (575 mg of nanoparticulate megestrol acetate formulation in 5 ml oral suspension) was administered in the first period. Reference Treatment B (800 mg of megestrol acetate (Megace® by Bristol Myers Squibb Co.) in 20 ml oral suspension) was administered in the second period. Treatment C (625 mg of nanoparticulate megestrol acetate formulation in 5 ml oral suspension) was administered in the third period. Treatment D (675 mg of nanoparticulate megestrol acetate formulation in 5 ml oral suspension) was administered in the fourth period.

Table 14 provides the formulations of Treatments A, C and D.

TABLE 14

Formulations of Nanoparticulate Megestrol Acetate Oral Suspensions

| | Dosage | | | | | |
|---|---|---|---|---|---|---|
| | 115 mg/mL | | 125 mg/mL | | 135 mg/mL | |
| | FINAL AMOUNTS | | | | | |
| | Weight (g) | Conc. (mg/mL) | Weight (g) | Conc. (mg/mL) | Weight (g) | Conc. (mg/mL) |
| Megestrol Acetate | 37,500.0 | 115.00 | 37,500.0 | 125.00 | 37,500.0 | 135.00 |
| HPMC | 7,500.0 | 23.00 | 7,500.0 | 25.00 | 7,500.0 | 27.00 |
| Docusate Sodium | 375.0 | 1.15 | 375.0 | 1.25 | 375.0 | 1.35 |
| Sodium Benzoate | 530.4 | 1.63 | 481.4 | 1.60 | 439.7 | 1.58 |
| Sodium Citrate Dihydrate | 26.5 | 0.08 | 24.0 | 0.08 | 22.0 | 0.08 |
| Citric Acid Monohydrate | 397.8 | 1.22 | 361.1 | 1.20 | 329.8 | 1.19 |
| Sucrose | 15,473.0 | 47.45 | 14,044.0 | 46.81 | 12,826.7 | 46.18 |
| Lemon Flavor | 123.8 | 0.38 | 112.4 | 0.37 | 102.6 | 0.37 |
| Lime Flavor | 123.8 | 0.38 | 112.4 | 0.37 | 102.6 | 0.37 |
| Water | 277,080.1 | — | 251,489.7 | — | 229,690.5 | — |
| TOTAL (Weight, g) | 339,130.4 | | 312,000.0 | — | 288,888.9 | — |
| TOTAL (volume, L) | 326.1 | | 300.0 | — | 277.8 | — |

The nanoparticulate megestrol acetate formulations were prepared by milling a concentrated dispersion of the drug substance followed by dilution to yield the final products. Hydroxypropyl methylcellulose and docusate sodium were used as stabilizing agents. The formulations were processed in a NanoMill-10 horizontal media mill (Netzsch USA) for 20 hours. The attrition media used was 500 μm crosslinked polystyrene (PolyMill™-500). The dispersion further comprised 0.13% sodium benzoate, 0.01% sodium citrate dihydrate, and 0.1% citric acid monohydrate. Milled dispersion was diluted to final megestrol acetate concentrations of 115 mg/mL (575 mg/5 mL), 125 mg/mL (625 mg/5 mL) and 135 mg/mL (675 mg/5 mL). The final compositions additionally contained sweetening and flavoring agents.

Particle size determinations were performed on a Malvern Mastersizer 2000 instrument. The particle size distributions of the nanoparticulate megestrol acetate compositions are provided in Table 15.

TABLE 15

| Concentration (mg/mL) | Mean particle size (nm) | 50%< (nm) | 90%< (nm) |
|---|---|---|---|
| 115 | 144 | 130 | 234 |
| 125 | 144 | 127 | 237 |
| 135 | 145 | 131 | 236 |

In each period, subjects were confined from at least 11 hours prior to drug administration until after the 24.0 hour post-dose sample collection. After a supervised fast of at least 10 hours, subjects were fed a high-calorie meal containing about 800 to 1000 calories (approximately 150 calories from carbohydrates and 500-600 calories from fat). The meal consisted of two eggs fried in butter, two slices of toast with butter, two strips of bacon, approximately 128 g of hash brown potatoes and 200 ml of whole milk. The meals in all four periods were identical. The meal was completed within 30 minutes, and subjects were dosed 30 minutes after starting the meal.

The suspensions of Treatments A, B, C and D were administered via Slip Tip syringe directly into the mouth and swallowed. The syringe was rinsed three (3) times with approximately 5 ml (Treatments A, C and D) or 20 ml (Treatment B) of water. Following drug administration, approximately 225 ml (Treatments A, C and D) or 180 ml (Treatment B) of water was ingested.

For each period, a total of 24 blood samples were drawn from each subject. Blood samples were collected in EDTA blood tubes prior to drug administration and 0.250, 0.500, 0.750, 1.00, 1.50, 2.00, 2.50, 3.00, 3.50, 4.00, 4.50, 5.00, 5.50, 6.00, 8.00, 12.0, 16.0, 20.0, 24.0, 36.0, 48.0, 72.0 and 96.0 hours post-dose (1×7 mL for each sampling time).

Table 16 below summarizes the pharmacokinetic data, while Table 17 provides the statistical comparisons of the treatments.

TABLE 16

| | | Pharmacokinetic Parameters | | | |
|---|---|---|---|---|---|
| | | Test-1 (Megtestrol Acetate 575 mg/5 mL (A)) | | Reference: (Megace 40 mg/mL (B)) | |
| Parameters | | Mean ± SD | CV (%) | Mean ± SD | Cv (%) |
| $AUC_{o-t}$ | (ng·h/mL) | 13657.52 ± 3900.50 | 28.56 | 16896.21 ± 4942.51 | 29.25 |
| $AUC_{o-inf}$ | (ng·h/mL) | 14743.33 ± 4451.31 | 30.19 | 18274.06 ± 5623.07 | 30.77 |
| $C_{max}$ | (ng/mL) | 1420.73 ± 420.79 | 2962 | 1400.66 ± 350.57 | 25.03 |
| $T_{max}$ | (h) | 3.75 ± 1.57 | 41.85 | 3.88 ± 1.02 | 26.38 |
| $T_{max}*$ | (h) | 4.50 ± 1.00 | — | 4.50 ± 1.00 | — |
| $K_{el}$ | (h$^{-1}$) | 0.0224 ± 0.0062 | 27.44 | 0.0238 ± 0.0054 | 22.84 |
| $T_{1/2\,el}$ | (h) | 32.78 ± 7.47 | 22.80 | 30.53 ± 6.66 | 21.80 |

TABLE 16-continued

Pharmacokinetic Parameters

| | | Test-2 (Megtestrol Acetate 625 mg/5 mL (C)) | | Test-3 (Megestrol Acetate 675 mg/5 mL (D)) | |
|---|---|---|---|---|---|
| Parameters | | Mean ± SD | CV (%) | ± ± SD | Cv (%) |
| $AUC_{o-t}$ | (ng-h/mL) | 14682.37 ± 4844.60 | 33.00 | 15323.29 ± 4525.94 | 29.54 |
| $AUC_{o-inf}$ | (ng-h/mL) | 16081.76 ± 5563.09 | 34.59 | 16738.88 ± 5432.52 | 32.45 |
| $C_{max}$ | (ng/mL) | 1516.79 ± 389.01 | 25.65 | 1645.74 ± 455.71 | 27.69 |
| $T_{max}$ | (h) | 2.52 ± 1.60 | 63.52 | 3.13 ± 1.64 | 52.55 |
| $T_{max}*$ | (h) | 2.50 ± 3.50 | — | 3.50 ± 3.00 | — |
| $K_{el}$ | ($h^{-1}$) | 0.0211 ± 0.0055 | 26.21 | 0.0211 ± 0.0054 | 25.64 |
| $T_{1/2\ el}$ | (h) | 34.75 ± 7.81 | 22.48 | 34.83 ± 8.12 | 23.30 |

*Median and interquartile ranges are presented.
$AUC_{o-t}$ (ng · h/ml) = Area under the curve from time zero to the last measurable concentration
$AUC_{o-inf}$ (ng · h/ml) = Area under the curve from time zero to infinity
$C_{max}$ (ng/ml) = Maximum plasma concentration
$T_{max}$ (h) = Time to occurrence of $C_{max}$
$t_{1/2\ el}$ (h) = elimination half-life
$K_{el}$ (1/h) = elimination rate constant

TABLE 17

Treatment Comparisons

| Statistical Analysis (ANOVA) | Treatment Comparisons | Ratio[1] | 90% Geometric CL[2] Lower | Upper | Intra-Subject CV |
|---|---|---|---|---|---|
| $AUC_{0-t}$ | Megestrol Actate 575 mg/5 mL (A) vs Megace 40 mg/mL (B) | 81.06% | 78.20% | 84.03% | 8.82% |
| | Megestrol Acetate 625 mg/5 mL (C) vs Megace 40 mg/mL (B) | 86.29% | 83.24% | 89.45% | |
| | Megestrol Acetate 675 mg/5 mL (D) vs Megace 40 mg/mL (B) | 90.63% | 87.43% | 93.95% | |
| $AUC_{0-inf}$ | Megestrol Acetate 575 mg/5 mL (A) vs Megace 40 mg/mL (B) | 80.92% | 77.95% | 84.00% | 9.16% |
| | Megestrol Acetate 625 mg/5 mL (C) vs Megace 40 mg/mL (B) | 87.33% | 84.12% | 90.65% | |
| | Megestrol Acetate 675 mg/5 mL (D) vs Megace 40 mg/mL (B) | 91.31% | 87.96% | 94.79% | |
| $C_{max}$ | Megestrol Acetate 575 mg/5 mL (A) vs Megace 40 mg/mL (B) | 100.62% | 94.10% | 107.69% | 16.51% |
| | Megestrol Acetate 625 mg/5 mL (C) vs Megace 40 mg/mL (B) | 108.18% | 101.17% | 115.69% | |
| | Megestrol Acetate 675 mg/5 mL (D) vs Megace 40 mg/mL (B) | 116.72% | 109.15% | 124.82% | |

Figure 4:
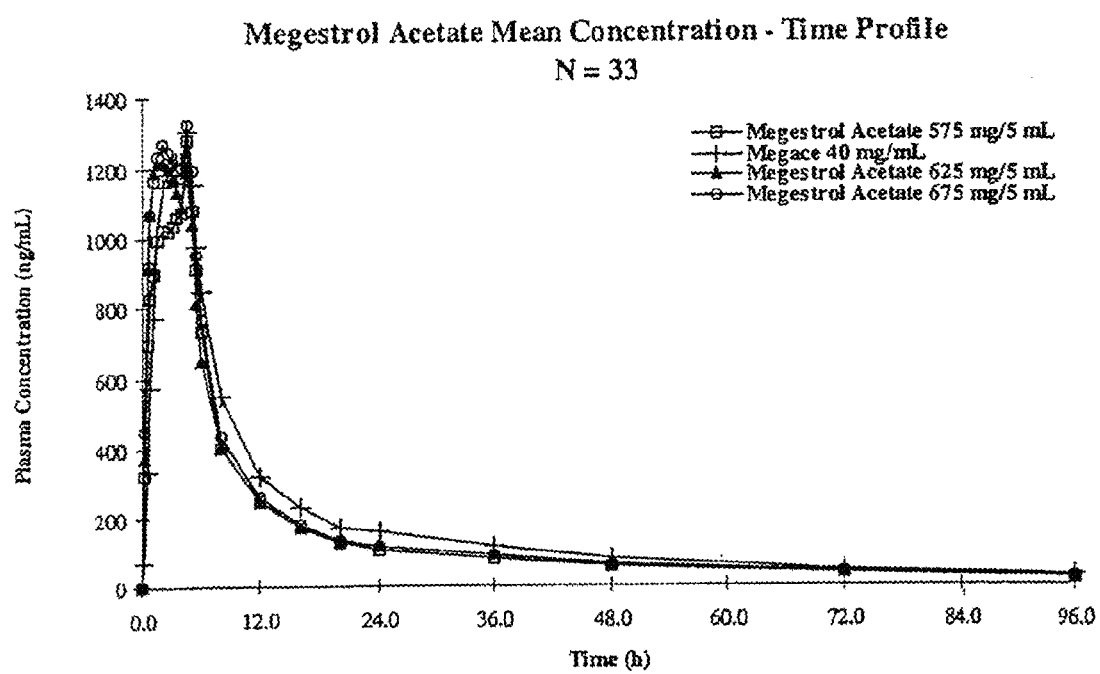
FIG. 4: The figure graphically shows the comparative bioavailability (via plasma concentration (ng/mL)) of several nanoparticulate megestrol compositions (575 mg/5 ml, 625 mg/5 ml and 675 mg/5 ml) versus a conventional megestrol acetate marketed by Bristol Myers Squibb.
Figure 5:
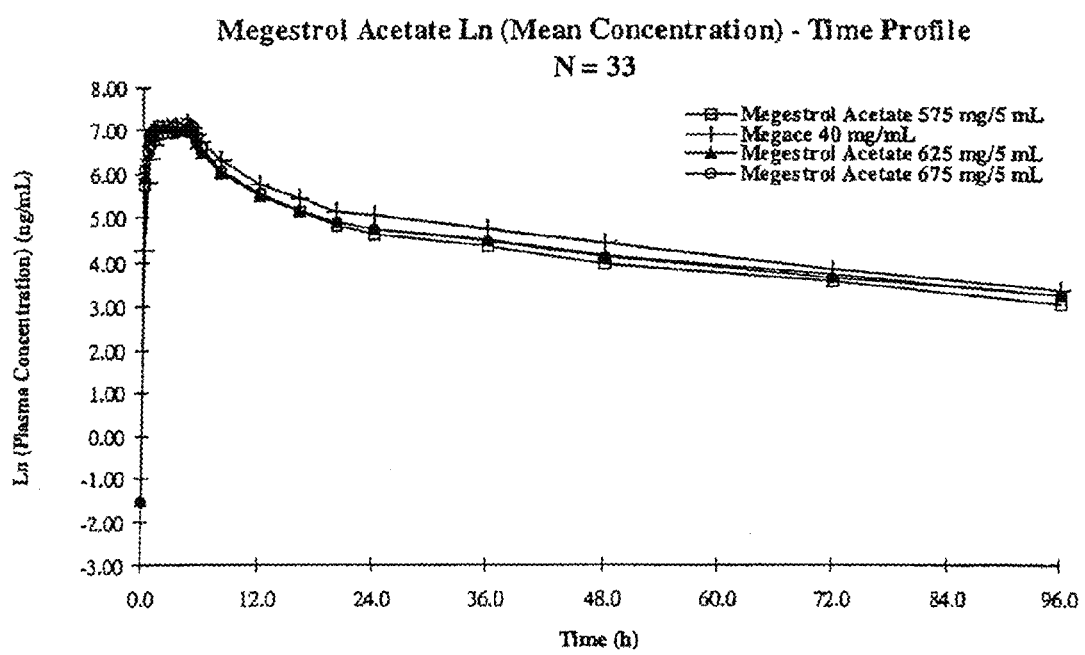
FIG. 5: The figure graphically shows on a natural log scale the comparative bioavailability (via plasma concentration (ng/mL)) of several nanoparticulate megestrol compositions (575 mg/5 ml, 625 mg/5 ml and 675 mg/5 ml) versus a conventional megestrol acetate marketed by Bristol Myers Squibb.

[1]Calculated using least-squares means
[2]90% Geometric Confidence Interval using ln-transformed data Tables 16 and 17 demonstrate that Treatments A, C, and D produced similar pharmakinetics as Treatment B. FIGS. 4 and 5 show that Treatments A, C and D produce similar concentration-time curves as Treatment B.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A method of increasing the body mass in a human patient suffering from anorexia, cachexia, or loss of body mass comprising administering to the human patient a megestrol acetate formulation, wherein:

(a) the megestrol acetate formulation is a dose of about 40 mg to about 800 mg in about a 5 mL dose of an oral suspension;

(b) the megestrol acetate formulation comprises megestrol acetate particles, wherein about 80% of the particles are between about 250 nm and about 50 nm, and at least one surface stabilizer is associated with the surface of the megestrol acetate particles; and (c) the administration is once daily;

wherein after a single administration in a human subject of the formulation there is no substantial difference in the $C_{max}$ of megestrol when the formulation is administered to the subject in a fed versus a fasted state, wherein fasted state is defined as the subject having no food within at least the previous 10 hours, and wherein fed state is defined as the subject having a high-calorie meal within approximately 30 minutes of dosing.

2. The method of claim 1, wherein about 80% of the particles are between about 230 nm and about 70 nm.

3. The method of claim 1, wherein the anorexia, cachexia or loss of body mass is associated with a diagnosis of HIV or AIDS in the human patient.

4. The method of claim 1, wherein the anorexia, cachexia or loss of body mass is associated with a diagnosis of cancer in the human patient.

5. The method of claim 1, wherein there is a difference in the mean $T_{max}$ for the nanoparticulate megestrol acetate formulation when administered in fed versus fasted states, and that difference is selected from the group consisting of less than about 100%, less than about 90%, less than about 80%, less than about 70%, less than about 60%, less than about 50%, less than about 40%, less than about 30%, less than about 20%, less than about 15%, less than about 10%, less than about 5%, and less than about 3%.

6. The method of claim 1, wherein the formulation exhibits a mean $C_{max}$, selected from the group consisting of greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130% greater than about 140%, and greater than about 150% of the mean $C_{max}$ exhibited by a standard commercial, non-nanoparticulate composition of megestrol, administered at the same dosage.

7. The method of claim 1, wherein there is a difference in absorption (AUC) when the formulation is administered in fed versus fasted states, and the difference is selected from the group consisting of less than about 35%, less than about 30%, less than about 25%, less than about 20%, less than about 15%, less than about 10%, less than about 5%, and less than about 3%.

8. The method of claim 1, wherein a maximum blood plasma concentration of megestrol is attained in about 1 hour or less after administration of the megestrol acetate formulation in fasting subjects.

9. The method of claim 1, wherein a maximum blood plasma concentration of megestrol of at least about 700 ng/ml is obtained.

10. The method of claim 9, wherein the maximum blood plasma concentration of megestrol is at least about 700 ng/ml and is attained in less than 5 hours after administration of the megestrol acetate formulation.

11. The method of claim 1, wherein the maximum blood plasma concentration of megestrol is at least about 400 ng/ml and is attained in less than 5 hours after administration of the megestrol acetate formulation.

12. The method of claim 1, wherein a mean $C_{max}$ of about 300 ng/ml to about 2000 ng/ml is obtained after a single administration of the formulation in the human subject in a fasted state.

13. The method of claim 1, wherein the surface stabilizer is selected from the group consisting of nonionic surfactants, cationic surfactants, ionic surfactants, and zwitterionic surfactants.

14. The method of claim 1, wherein the surface stabilizer is selected from the group consisting of hydroxypropyl methylcellulose, hydroxypropylcellulose, polyvinylpyrrolidone, sodium lauryl sulfate, dioctylsulfosuccinate, polyoxyethylene alkyl etherspolyoxyethylene sorbitan fatty acid esters, 4-(1,1,3,3-tetramethylbutyl)-phenol polymer with ethylene oxide and formaldehyde, lysozyme, and random copolymers of vinyl pyrrolidone and vinyl acetate.

15. The method of claim 14, wherein the surface stabilizer is selected from the group consisting of hydroxypropyl methylcellulose, dioctylsulfosuccinate, and a combination thereof.

16. A method of increasing the body mass in a human patient suffering from anorexia, cachexia, or loss of body mass comprising administering to the human patient a megestrol acetate formulation, wherein:
(a) the megestrol acetate formulation is a dose of about 40 mg to about 800 mg in about a 5 mL dose of an oral suspension;
(b) the megestrol acetate formulation comprises megestrol acetate particles, wherein about 90% of the particles are less than or equivalent to about 250 nm, and about 10% of the particles are less than or equivalent to about 50 nm, and at least one surface stabilizer is associated with the surface of the megestrol acetate particles; and
(c) the administration is once daily;
wherein after a single administration in a human subject of the formulation there is no substantial difference in the $C_{max}$ of megestrol when the formulation is administered to the subject in a fed versus a fasted state,
wherein fasted state is defined as the subject having no food within at least the previous 10 hours, and
wherein fed state is defined as the subject having a high-calorie meal within approximately 30 minutes of dosing.

17. The method of claim 16, wherein about 90% of the particles are less than or equivalent to about 230 nm, and about 10% of the particles are less than or equivalent to about 70 nm.

18. The method of claim 16, wherein the anorexia, cachexia or loss of body mass is associated with a diagnosis of HIV or AIDS in the human patient.

19. The method of claim 16, wherein the anorexia, cachexia or loss of body mass is associated with a diagnosis of cancer in the human patient.

20. The method of claim 16, wherein the surface stabilizer is selected from the group consisting of nonionic surfactants, cationic surfactants, ionic surfactants, and zwitterionic surfactants.

21. The method of claim 16, wherein the surface stabilizer is selected from the group consisting of hydroxypropyl methylcellulose, hydroxypropylcellulose, polyvinylpyrrolidone, sodium lauryl sulfate, dioctylsulfosuccinate, polyoxyethylene alkyl etherspolyoxyethylene sorbitan fatty acid esters, 4-(1,1,3,3-tetramethylbutyl)-phenol polymer with ethylene oxide and formaldehyde, lysozyme, and random copolymers of vinyl pyrrolidone and vinyl acetate.

22. The method of claim 21, wherein the surface stabilizer is selected from the group consisting of hydroxypropyl methylcellulose, dioctylsulfosuccinate, and a combination thereof.

23. A method of increasing the body mass in a human patient suffering from anorexia, cachexia, or loss of body mass comprising administering to the human patient a megestrol acetate formulation, wherein:
(a) the megestrol acetate formulation is a dose of about 40 mg to about 800 mg in about a 5 mL dose of an oral suspension;
(b) the megestrol acetate formulation comprises megestrol acetate particles, wherein about 90% of the particles have a size less than or equivalent to about 250 nm and about 90% of particles have a size greater than or equivalent to about 50 nm, and at least one surface stabilizer is associated with the surface of the megestrol acetate particles; and
(c) the administration is once daily;
wherein after a single administration in a human subject of the formulation there is no substantial difference in the $C_{max}$ of megestrol when the formulation is administered to the subject in a fed versus a fasted state, wherein fasted state is defined as the subject having no food within at least the previous 10 hours, and wherein fed state is defined as the subject having a high-calorie meal within approximately 30 minutes of dosing.

24. The method of claim 23, wherein about 90% of the particles have a size less than or equivalent to about 230 nm and about 90% of particles have a size greater than or equivalent to about 70 nm.

25. The method of claim 23, wherein the anorexia, cachexia or loss of body mass is associated with a diagnosis of HIV or AIDS in the human patient.

26. The method of claim 23, wherein the anorexia, cachexia or loss of body mass is associated with a diagnosis of cancer in the human patient.

27. The method of claim 23, wherein the surface stabilizer is selected from the group consisting of nonionic surfactants, cationic surfactants, ionic surfactants, and zwitterionic surfactants.

28. The method of claim 23, wherein the surface stabilizer is selected from the group consisting of hydroxypropyl methylcellulose, hydroxypropylcellulose, polyvinylpyrrolidone, sodium lauryl sulfate, dioctylsulfosuccinate, polyoxyethylene alkyl etherspolyoxyethylene sorbitan fatty acid esters, 4-(1,1,3,3-tetramethylbutyl)-phenol polymer with ethylene oxide and formaldehyde, lysozyme, and random copolymers of vinyl pyrrolidone and vinyl acetate.

29. The method of claim 19, wherein the surface stabilizer is selected from the group consisting of hydroxypropyl methylcellulose, dioctylsulfosuccinate, and a combination thereof.

* * * * *